(12) United States Patent
Bratton et al.

(10) Patent No.: US 6,316,449 B1
(45) Date of Patent: Nov. 13, 2001

(54) CHEMOKINE RECEPTOR ANTAGONISTS

(75) Inventors: Larry Don Bratton, Whitmore Lake; Steven Robert Miller, Ann Arbor; Bruce David Roth, Plymouth; Bharat Kalidas Trivedi; Paul Charles Unangst, both of Ann Arbor, all of MI (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/558,267

(22) Filed: Apr. 25, 2000

Related U.S. Application Data

(60) Provisional application No. 60/142,755, filed on Jul. 8, 1999.

(51) Int. Cl.$^7$ .................. A61K 31/150; A61K 31/505; C07D 401/00; C07D 239/02; C07D 239/72
(52) U.S. Cl. ............... 514/252.04; 514/256; 514/259; 544/238; 544/311; 544/283; 544/287
(58) Field of Search .............. 546/52, 51; 514/280, 514/256, 252.04, 259; 544/238, 283, 311, 287

(56) References Cited

U.S. PATENT DOCUMENTS

| | | | |
|---|---|---|---|
| 3,139,428 | * 6/1964 | Shavel et al. | |
| 3,193,555 | 7/1965 | Shavel, Jr. et al. | 260/287 |
| 3,291,800 | * 12/1966 | Shavel, Jr. et al. | 260/288 |
| 3,487,086 | 12/1969 | Shavel, Jr. et al. | 260/286 |

FOREIGN PATENT DOCUMENTS 1006882  6/1965  (GB).

OTHER PUBLICATIONS

Schall and Bacon, "Chemokines, leukocyte trafficking, and inflammation", *Current Opinion in Immunology*, vol. 6, 1994, pp 865–873.

Gerard and Gerard, "The pro–inflammatory seven–transmembrane segment receptors of the leukocyte", *Current Opinion in Immunology*, vol. 6, 1994, pp 140–145.

*Ann. Khim. Zh.*, vol. 31, 1978, pp 363–;—not available as of Aug. 10, 2000.

*Ann. Khim. Zh.*, vol. 27, 1974, pp 978–;—not available as of Aug. 10, 2000.

Alkhatib et al., "CC CKR5: A RANTES, MIP–1, MIP–1 Receptor as a Fusion Cofactor for Macrophage–Tropic HIV–1", *Science*, vol. 272, 1996, pp 1955–1958.

Springer, "Adhesion receptors of the immune system", *Nature*, vol. 346, 1990, pp 425–434.

Lawrence and Springer, "Leukocytes Roll on a Selectin at Physiologic flow Rates: Distinction from and Prerequisite for Adhesion through Integrins", *Cell*, vol. 65, 1991, pp 859–873.

Nourshargh and Williams, "Evidence that a receptor–operated event on the neutrophil mediates neutrophil accumlation in vivo", *The Journal of Immunology*, vol. 145, No. 8, 1990, pp 2633–2638.

Butcher, "Leukocyte–Endothelial Cell Recognition: Three (or More) Steps to Specificity and Diversity", *Cell*, vol. 67, 1991, pp 1033–1036.

Ernst et al., "Biochemical and Biologic Characterization of Murine Monocyte Chemoattractant Protein–1", *Journal of Immunology*, vol. 152, 1994, pp 3541–3549.

Colditz, "Desensitisation mechanisms regulating plasma leakage and neutrophil emigration", Gordon (ed.), *Vascular endothelium: Interactions with circulating cells*, 1991 Elsevier Science Publishers B.V., Chapter 10, pp 175–187.

Spangrude et al., "Inhibition of lymphocyte and neutrophil chemotaxis by pertussis toxin", *The Journal of Immunology*, vol. 135, No. 6, 1985, pp 4135–4143.

Sekido et al., "Prevention of lung reperfusion injury in rabbits by a monoclonal antibody against interleukin–8", *Nature*, vol. 365, 1993, pp 654–657.

Baggiolini et al., "Interleukin–8 and Related Chemotactic Cytokines—CXC and CC Chemokines", *Adv. Immunol.*, vol. 55, 1994, pp 97–179.

Oppenheim et al., "Properties of the novel proinflammatory supergene "intercrine" cytokine family", *Annu. Rev. Immunol.*, vol. 9, 1991, pp 617–648.

Miller and Krangel, "Biology and Biochemistry of the Chemokines: A Family of Chemotactic and Inflammatory Cytokines", *Critical Reviews in Immunology*, vol. 12(1,2), 1992, pp 17–46.

Springer, "Traffic Signals for Lymphocyte Recirculation and Leukocyte Emigration: The Multistep Paradigm", *Cell*, vol. 76, 1994, pp 301–314.

(List continued on next page.)

Primary Examiner—Alan L. Rotman
(74) Attorney, Agent, or Firm—Lahive & Cockfield, LLP; Elizabeth A. Hanley

(57) ABSTRACT

The instant invention is a series of compounds which are MCP-1 receptor antagonists of Formula I

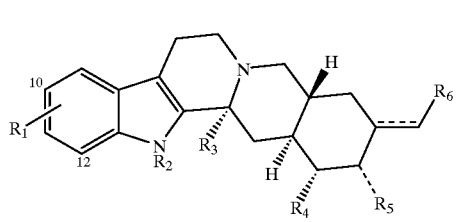

Also included in the invention are intermediates and processes for the preparation of the compounds as well as methods of using the compounds as agents for the treatment of atherosclerosis, chronic and acute inflammatory disease, chronic and acute immune disorders and transplant rejection as well as for preventing infection by HIV, treating infection by HIV, delaying the onset of AIDS, or treating AIDS.

33 Claims, No Drawings

OTHER PUBLICATIONS

CA 73:13005n.

CA 100:180597q.

De la Iglesia et al., "The Significance of Ultrastructural Mitochondrial Changes in Toxicology", *Proc. Eur. Soc. Study Drug Toxicity*, vol. 10, 1969, pp 101–121.

Frolov et al., *Izv. Vyssh. Uchebn. Zaved., Khim. Khim. Teknol.*, vol. 27, No. 2, 1984, pp 210–214 (Russian language).

Zinnes et al., "Yohimbane Derivatives. I. The Preparation of 3–Substituted Yohimbane Derivatives", *J. Org. Chem.*, vol. 30, 1965, pp 105–112.

von Strandtmann et al., "Yohimbane Derivatives. II. The Synthesis and Psychopharmacological Properties of Yohimbane Derivatives with Halogen Substituents in Ring E", *J. Med. Chem.*, vol. 8, 1965, pp 338–341.

von Strandtmann et al., "The Preparation and Optical Rotary Dispersion of 7–Benzyl–7H–yohimbanes", *J. Org. Chem.*, vol. 31, 1966, pp 4202–4204.

Aimi et al., "Introduction of substituents to $C_3$ of yohimbinoid skeleton", *Heterocycles*, vol. 5, 1976, pp 267–273.

Merlini, et al., "Some Models for the Synthesis of Indole Alkaloids", *Gazz. Chim. Ital.*, vol. 105, 1975, pp 339–348.

CA 54:15420e.

Cordell and Farnsworth, "Catharanthus Alkaloids XXXII: Isolation of Alkaloids from *Catharanthus trichophyllus* Roots and Structure Elucidation of Cathaphylline", *J. Pharm. Sci.*, vol. 65, No. 3, 1976, pp 366–369.

Hakkesteegt, "A Study on the decomposition of reserpine, II", *Pharm. Weekblad*, vol. 105, 1970, pp 829–841.

Hakkesteegt, "A study on the decomposition of reserpine, I", *Pharm. Weekblad*, vol. 105, 1970, pp 801–814.

Yamanaka et al., *Chem. Pharm. Bull.*, vol. 32, No. 2, 1984, pp 818–821.

Murphy et al., "The Molecular Biology of Leukocyte Chemoattractant Receptors", *Annu. Rev. Immunol.*, vol. 12, 1994, pp 593–633.

Cocchi et al., "Identification of RANTES, MIP–1 , and MIP–1 as the Major HIV–Suppressive Factors Produced by $CD8^+T$ Cells", *Science*, vol. 270, 1995, pp 1811–1815.

Feng et al., "HIV–1 Entry Cofactor: Functional cDNA Cloning of a Seven–Transmembrane, G Protein–Coupled Receptor", *Science*, vol. 272, 1996, pp 872–877.

Choe et al., "The –Chemokine Receptors CCR3 and CCR5 Facilitate Infection by Primary HIV–1 Isolates", Cell, vol. 85, 1996, pp 1135–1148.

Alkhatib et al., "CC CKR5: A RANTES, MIP–1 , MIP–1 Receptor as a Fusion Cofactor for Macrophage–Tropic HIV–1", *Science*, vol. 272, 1996, pp 1955–1958.

Doranz et al., "A Dual–Tropic Primary HIV–1 Isolate That Uses Fusin and the –Chemokine Recepotrs CKR–5, CKR–3, and CKR–2b as Fusion Cofactors", *Cell*, vol. 85, 1996, pp 1149–1158.

Deng et al., "Identification of a major co–receptor for primary isolates of HIV–1", *Nature*, vol. 381, 1996, pp 661–666.

Dragic et al., "HIV–1 entry into $CD4^+$cells is mediated by the chemokine receptor CC–CKR–5", *Nature*, vol. 381, 1996, pp 667–673.

Liu et al., "Homozygous Defect in HIV–1 Coreceptor Accounts for Resistance of Some Multiply–Exposed Individuals to HIV–1 Infection", *Cell*, vol. 86, 1996, pp 367–377.

Samson et al., "Resistance to HIV–1 Infection in caucasian individuals bearing mutant alleles of the CCR–5 chemokine receptor gene", *Nature*, vol. 382, 1996, pp 722–725.

Dean et al., "Genetic Restriction of HIV–1 Infection and Progression to AIDS by a Deletion Allele of the CKR5 Structural Gene", *Science*, vol. 273, 1996, pp 1856–1862.

Huang et al., "The role of a mutant CCR5 allele in HIV–1 transmission and disease progression", *Nature Medicine*, vol. 2, No. 11, 1996, pp 1240–1243.

Hechtman et al., "Inhibitor of Polymorphonuclear Leukocyte Accumulation at Sites of Acute Inflammation", *The Journal of Immunology*, vol. 147, No. 3, 1991, pp 883–892.

Huber et al., "Regulation of Transendothelial Neutrophil Migration by Endogenous Interleukin–8", *Science*, vol. 254, 1991, pp 99–102.

Carr et al., "Monocyte chemattractant protein 1 acts as a T–lymphocyte chemoattractant", *Proc. Natl. Acad. Sci. USA*, vol. 91, 1994, pp 3652–3656.

De la Iglesia, et. al., "Significance of ultrastructural mitochondrial changes in toxicology", CA Reference 73: 13005n, pp. 213–214, 1970.*

Nazarov, et al., "Adsorption of iron triad metal ions on a silicon dioxide hydrosol modified by molybdates", CA reference 100:180597q, p. 360, 1980.*

* cited by examiner

CHEMOKINE RECEPTOR ANTAGONISTS

This application claims the benefit of Ser. No. 60/142,755 expired, filed Jul. 8, 1999.

BACKGROUND OF THE INVENTION

U.S. Pat. No. 3,139,428 teaches compounds of formula

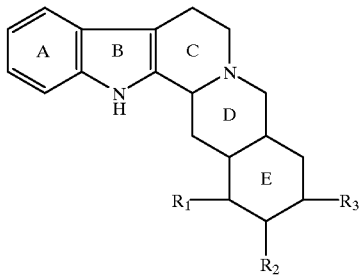

wherein $R_1$ is hydrogen, methyl, or $R_3$; $R_2$ is hydrogen, keto, hydroxyl or a radical of the formula —$OR_4$ in which $R_4$ is the acyl radical of an aliphatic carboxylic acid containing 2 to 6 carbon atoms such as acetyl, propionyl, butyryl, valeryl, hexanoyl and the like, benzoyl or benzoyl substituted with 1, 2, or 3 lower alkyl, halo or lower alkoxy groups, for example p-methylbenzoyl, m-methylbenzoyl, o-methylbenzoyl, 3,4-dimethylbenzoyl, p-chlorobenzoyl, p-fluorobenzoyl, o-bromobenzoyl, m-chlorobenzoyl, 2,4-dichlorobenzoyl, p-methoxybenzoyl, 3,4,5-trimethoxybenzoyl, 3,4-dimethoxybenzoyl and the like; and $R_3$ is =$CHR_5$ or —$CH_2R_6$ in which $R_5$ is lower alkyl, furyl, phenyl, phenyl lower alkyl such as benzyl, phenethyl, phenylpropyl and the like, phenyl lower alkenyl such as cinnamyl, phenylpropenyl, phenylbutenyl and the like, methylenedioxyphenyl, or phenyl nuclearly substituted with 1 or 2 halo, lower alkyl, lower alkoxy or nitro groups such as p-chlorophenyl, 3,4-dichlorophenyl, m-methylphenyl, o-bromophenyl, p-ethylphenyl, p-fluorophenyl, p-methoxyphenyl, o-methoxyphenyl, m-butoxyphenyl, p-nitrophenyl, 3,4-dinitrophenyl, 2,4-dinitrophenyl, o-nitrophenyl, m-nitrophenyl and the like, and $R^6$ is lower alkyl, furyl, phenyl, phenyl lower alkyl, methylenedioxyphenyl, or phenyl nuclearly substituted with 1 or 2 halo, lower alkyl, lower alkoxy or amino groups. The compounds are disclosed as useful as intermediates and as anti-inflammatory agents.

U.S. Pat. No. 3,291,800 teaches compounds of formula

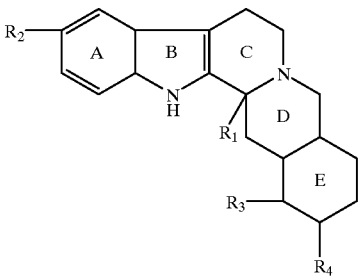

wherein $R_1$ represents lower alkyl such as methyl, ethyl, propyl, isopropyl, butyl, isobutyl and the like, aryl such as phenyl or aralkyl such as benzyl; $R_2$ represents hydrogen, lower alkyl such as methyl, ethyl, propyl, isopropyl and the like, lower alkoxy such as methoxy or ethoxy or acetyl; $R_3$ represents hydrogen or lower alkyl and $R_4$ represents hydrogen hydroxy or keto and to the nontoxic pharmaceutically acceptable acid addition and quaternary ammonium salts thereof. The compounds are disclosed as having pharmacological activity as analgesics, tranquilizers, and anti-inflammatory agents.

These patents are hereby incorporated by reference.

Migration of leukocytes from blood vessels into diseased tissues is important to the initiation of normal disease-fighting inflammatory responses. But this process, known as leukocyte recruitment, is also involved in the onset and progression of debilitating and life-threatening inflammatory and autoimmune diseases. The pathology of these diseases results from the attack of the body's immune system defenses on normal tissues. Thus, blocking leukocyte recruitment to target tissues in inflammatory and autoimmune disease would be a highly effective therapeutic intervention. The leukocyte cell classes that participate in cellular immune responses include lymphocytes, monocytes, neutrophils, eosinophils and basophils. In many cases, lymphocytes are the leukocyte class that initiates, coordinates, and maintains chronic inflammatory responses, and thus are generally the most important class of cells to block from entering inflammatory sites. Lymphocytes attract monocytes to the site, which, collectively with lymphocytes, are responsible for much of the actual tissue damage that occurs in inflammatory disease. Infiltration of lymphocytes and/or monocytes is responsible for a wide range of chronic, autoimmune diseases, and also organ transplant rejection. These diseases include, but are not limited to, rheumatoid arthritis, atherosclerosis, psoriasis, chronic contact dermatitis, inflammatory bowel disease, multiple sclerosis, sarcoidosis, idiopathic pulmonary fibrosis, dermatomyositis, skin pemphigoid and related diseases, (e.g., *pemphigus vulgaris, p. foliacious, p. erythematosis*), glomerulonephritides, vasculitides, hepatitis, diabetes, allograft rejection, and graft-versus-host disease.

This process, by which leukocytes leave the bloodstream and accumulate at inflammatory sites, and initiate disease, takes place in at least three distinct steps which have been described as (1) rolling, (2) activation/firm adhesion and (3) transendothelial migration (Springer T. A., *Nature* 1990;346:425–433; Lawrence and Springer, *Cell* 1991;65:859–873; Butcher E. C., *Cell* 1991;67:1033–1036). The second step is mediated at a molecular level by chemoattractant receptors. Chemoattractant receptors on the surface of leukocytes bind chemoattractant cytokines secreted by cells at the site of damage or infection. Receptor binding activates leukocytes, increases the adhesiveness of the adhesion molecules that mediate transendothelial migration, and promotes directed migration of the cells toward the source of the chemoattractant cytokine.

A recent discovery is the existence of a large family (>20 members) of structurally homologous chemoattractant cytokines, approximately 8 to 10 kD in size. These molecules share the ability to stimulate directed cell migration (chemotaxis) and have been collectively called "chemokines," a contraction of chemotactic cytokines. Each chemokine contains four cysteine residues (C) and two internal disulfide bonds. Chemokines can be grouped into two subfamilies, based on whether the two amino terminal cysteine residues are immediately adjacent (C—C family) or separated by one amino acid (C—X—C family). These differences correlate with the organization of the two subfamilies into separate gene clusters. Within each gene cluster, the chemokines typically show sequence similarities between 25% to 60%.

The chemokines of the C—X—C subfamily, such as interleukin-8, are produced by a wide range of cell types and act predominantly on neutrophils as mediators of acute inflammation. Chemokines of the C—C subfamily are also produced by a wide variety of cell types. These molecules act predominantly on subsets of mononuclear inflammatory cells. Currently there are at least six C—C chemokines with known chemotactic activity for human monocytes and/or T cells, including MCP-1, MCP-2, MCP-3, MIP-1α, MIP-1β, and RANTES. This suggests there may be a high degree of redundancy in chemoattractant pathways. In addition, most C—C chemokines are chemotactic for more than one cell type. For examples, RANTES (regulated on activation, normal T cell expressed and secreted) acts on memory $CD4^+$ T cells, eosinophils, and monocytes. Monocyte chemoattractant protein-1 (MCP-1), another C—C chemokine, acts on monocytes, activated "memory" T cells and on basophils. MCP-1 is also a potent secretogogue of inflammatory mediators for monocytes and basophils.

Five C—C chemokine receptors have recently been characterized (CCRR1–5 or CCR1–CCR5), and all of these belong to the seven transmembrane spanning G protein-coupled receptor family. Each of these receptors mediates the binding and signaling of more than one chemokine. For example, the CCR1 receptor binds both MIP-1α and RANTES. There are 2 receptors which bind MCP-1, CCR2 (with alternately spliced forms, 2A and 2B) and CCR4. CCR2 is also known to mediate binding and signaling of MCP-3. The CCR4 receptor binds and signals, in addition to MCP-1, with RANTES and MIP-1α. Which of these is responsible for the MCP-1 mediated recruitment of monocytes and T cells is not known.

In agreement with the observation that lymphocyte emigration into inflammatory sites is usually accompanied by emigration of monocytes, MCP-1 is expressed at sites of antigen challenge and autoimmune disease. However, analyses of human inflammatory lesions with antibodies to other chemokines show RANTES, MIP-1I, MIP-1θ and MCP-3 to be present as well. Injection of MCP-1 into skin sites in mice provokes only a mild monocytic infiltrate or no infiltrate at all (Ernst C. A. et al., *J. Immunol.* 1994;152:3541–3544). Whether these results reflect redundant and complex recruitment pathways has not been resolved. MCP-1 and MCP-3 may play a role in allergic hypersensitivity disease. This is suggested by the observation that MCP-1 lacking the amino terminal glutamic acid loses the ability to stimulate basophil mediator release and acquires activity as an eosinophil chemoattractant.

Chemokines of both subfamilies may bind to heparan sulfate proteoglycans on the endothelial cell surface, and may function principally to stimulate haptotaxis of leukocytes that attach to cytokine-activated endothelium through induced adhesion molecules. Additionally, MCP-1 has been reported to selectively activate the β1 integrin family of leukocyte adhesion molecule, suggesting a role in leukocyte interactions with the extracellular matrix. Hence, MCP-1 may not only trigger the initial arrest and adhesion of monocytes and T cells, but may also act to guide their migration in extravascular space.

Chemoattractants appear to be required for transendothelial migration in vitro and in vivo and can induce all steps required for transmigration in vivo. Injection of neutrophil chemoattractants into skin or muscle leads to robust emigration of neutrophils from the vasculature and accumulation at the injection site (Colditz, 1991). Pretreatment of neutrophils with pertussis toxin inhibits emigration into inflammatory sites (Spangrude et al., 1985; Nourshargh and Williams, 1990). Moreover, MAb to IL-8 markedly inhibits neutrophil emigration in inflammation (Sekido et al., 1993).

Neutrophil chemoattractants injected into the same skin site hours apart will stimulate neutrophil accumulation the first time but not the second time, whereas a second injection into a distant site will stimulate accumulation at that site. This desensitization occurs for homologous chemoattractants only (Colditz, 1991) or those that interact with the same receptor. Thus, chemoattractants can act on and homologously desensitize a cell type that is localized in tissue.

Chemokines mediate a range of proinflammatory effects on leukocytes, such as chemotaxis, degranulation, and intigran activation (Baggiolini et al., *Adv. Immunol.*, 1994;55:97–179; Oppenheim et al., *Annu. Rev. Immunol.*, 1991; 9:617–48; Miller et al., *Crit. Rev. Immunol.*, 1992;12:17–46). These effects are mediated by binding to the seven-transmembrane-spanning G-protein coupled receptors (Baggiolini et al., *Adv. Immunol.*, 1994;55:97–179; Murphy, *Annu. Rev. Immunol.*, 1994;12:593–633; Schall et al., *Curr. Opin. Immunol.*, 1994;6:865–73; Gerard et al., *Curr. Opin. Immunol.*, 1994;6;140–5; Mackay, *Curr. Bio.*, In press). Chemokine receptors also serve as coreceptors for HIV-1 entry into cells. This came from observations that RANTES, MIP-1α, and MIP-1β suppressed infection of susceptible cells in vitro by macrophage-tropic primary HIV-1 isolates (Cocchi et al., *Science* (Wash. D.C.), 1995;270:1811–5). The chemokine receptor CXCR-4 was found to support infection and cell fusion of $CD4^+$ cells by laboratory-adapted, T-tropic HIV-1 strains (Feng et al., *Science* (Wash. D.C.), 1996;272:872–7). CCR-5, a RANTES, MIP-1α, and MIP-1β receptor, was subsequently identified as the principle coreceptor for primary macrophage-tropic strains (Choe et al., *Cell*, 1996;85: 1135–48; Alkhatib et al., *Science* (Wash. D.C.), 1996;272: 1955–8; Doranz et al., *Cell*, 1996;85: 1149–58; Deng et al., *Nature* (Lond.) 1996;381:661–6; Dragic et al., *Nature* (Lond.), 1996;381:667–3). The importance of CCR-5 for HIV-1 transmission was underscored by the observation that certain individuals who had been repeatedly exposed to HIV-1 but remained uninfected had a defect in CCR-5 expression (Liu et al., *Cell*, 1996; 86:367–77; Samson et al., *Nature* (Lond.), 1996;382:722–5; Dean et al., *Science* (Wash. D.C.), 1996;273:1856–62; Huang et al., *Nature Med.*, 1996;2:1240–3). These noninfectable individuals were found to be homozygous for a defective CCR-5 allele that contains an internal 32-base pair deletion (CCR-5 Δ32). The truncated protein encoded by this gene is apparently not expressed at the cell surface. CCR-5 Δ32 homozygous individuals comprise ~1% of the Caucasian population and heterozygous individuals comprise ~20%. In studies of about 2700 HIV-1 infected individuals, no Δ32 homozygotes were found. Individuals who are heterozygous for Δ32 CCR-5 allele have been shown to progress more slowly to AIDS than wild-type homozygous individuals (Samson et al., *Nature* (Lond.), 1996;382:722–5; Dean et al., *Science* (Wash. D.C.), 1996;273:1856–62; Huang et al., *Nature Med.*, 1996;2:1240–3). Thus, the identity of CCR-5 as the principle coreceptor for primary HIV isolates provides an opportunity to understand disease pathogenesis, and more importantly to identify a new avenue for the treatment of HIV-1 infection.

Chemoattractants impart directionality to leukocyte migration. By contrast with intradermal injection, intravascular injection of IL-8 does not lead to emigration (Hechtman et al., 1991). Cytokine-stimulated endothelial monolayers grown on filters secrete IL-8 into the underlying collagen layer. Neutrophils added to the apical compartment emigrate into the basilar compartment, but not when the IL-8 gradient is disrupted by addition of IL-8 to the apical compartment (Huber et al., 1991).

The endothelium may present chemoattractants to leukocytes in a functionally relevant way, as well as providing a permeability barrier that stabilizes the chemoattractant gradient. Since leukocytes, responding to specific antigen or inflammatory signals in tissue, may signal emigration of further leukocytes into the site, a chemoattractant was sought in material secreted by mitogen-stimulated mononuclear cells (Carr et al., 1994). Purification to homogeneity guided by a transendothelial lymphocyte chemotaxis assay revealed that monocyte chemoattractant protein 1 (MCP-1), previously thought to be solely a monocyte chemoattractant, is a major lymphocyte chemoattractant. An activated subset of memory lymphocytes respond to MCP-1. In the same assay, lymphocytes respond to RANTES and MIP-1α but less so than to MCP-1 (C—C chemokines) and not at all to IL-8 or IP-10 (C—X—C chemokines). This physiologically relevant assay suggests that C—C chemokines tend to attract both monocytes and lymphocytes. In agreement with the observation that lymphocyte emigration into inflammatory sites is accompanied by emigration of monocytes, MCP-1 is abundantly expressed at sites of antigen challenge and autoimmune disease (Miller and Krangel, 1992) and, together with other chemokines, is an excellent candidate to provide the step 2 signal required to activate integrin adhesiveness and emigration of lymphocytes in vivo. (Traffic Signals for Lymphocyte Recirculation and Leukocyte Emigration: The Multistep Paradigm; Springer, Cell 1994;76: 301–314).

We have surprisingly found the compounds of the invention are MCP-1 receptor antagonists and are capable of inhibiting the binding of MCP-1 to its receptor. Surprisingly, the compounds block T cell migration in vitro, and more surprisingly still, have dramatic effects on the recruitment of inflammatory cells in multiple models of inflammatory diseases. Thus, these compounds are useful as agents for the treatment of inflammatory disease, especially those associated with lymphocyte and/or monocyte accumulation, such as arthritis, atherosclerosis and transplant rejection. In addition, these compounds can be used in the treatment of allergic hypersensitivity disorders such as asthma and allergic rhinitis characterized by basophil activation and eosinophil recruitment, as well as for the treatment of restenosis and chronic or acute immune disorders.

The importance of CCR-5 for HIV-1 transmission was underscored by the observation that certain individuals who had been repeatedly exposed to HIV-1 but remained uninfected had a defect in CCR-5 expression (Liu et al., Cell, 1996; 86:367–77; Samson et al., Nature (Lond.), 1996;382:722–5; Dean et al., Science (Wash. D.C.), 1996;273:1856–62; Huang et al., Nature Med., 1996;2:1240–3). These noninfectable individuals were found to be homozygous for a defective CCR-5 allele that contains an internal 32-base pair deletion (CCR-5 Δ32). The truncated protein encoded by this gene is apparently not expressed at the cell surface. CCR-5 Δ32 homozygous individuals comprise ~1% of the Caucasian population and heterozygous individuals comprise ~20%. In studies of about 2700 HIV-1 infected individuals, no Δ32 homozygotes were found. Individuals who are heterozygous for Δ32 CCR-5 allele have been shown to progress more slowly to AIDS than wild-type homozygous individuals (Samson et al., Nature (Lond.), 1996;382:722–5; Dean et al., Science (Wash. D.C.), 1996;273:1856–62; Huang et al., Nature Med., 1996;2:1240–3). Thus, the identity of CCR-5 as the principle coreceptor for primary HIV isolates provides an opportunity to understand disease pathogenesis, and more importantly to identify a new avenue for the treatment of HIV-1 infection.

SUMMARY OF THE INVENTION

The invention is a novel compound of Formula I:

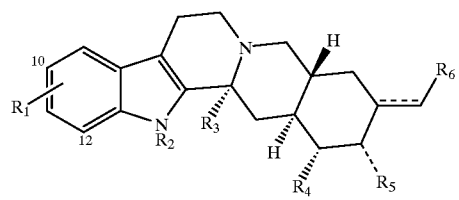

I or a pharmaceutically acceptable salt thereof wherein $R_1$, $R_2$, $R_3$, $R_4$, $R_5$, and $R_6$ are as described below.

The instant invention is also a method of inhibiting the binding of MCP-1 to its receptor comprising administering a therapeutically effective amount of a compound of Formula I above. The compounds are also useful for modulation of the CCR-5 chemokine receptor activity.

The compounds of Formula II

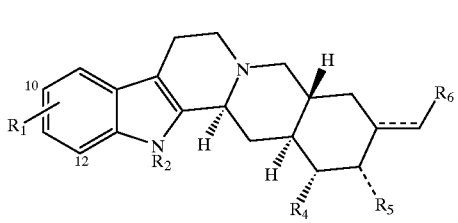

II are useful in treating atherosclerosis, pain, restenosis, immune disorders, preventing transplant rejection, treating virus, HIV, AIDS and for modulation of the CCR-5 chemokine receptor activity.

The compounds of Formula I are useful in the treatment of atherosclerosis, chronic and acute inflammatory disease, chronic and acute immune disorders, and transplant rejection in mammals in need of such treatment. The compounds are also useful for preventing infection by HIV, treating infection by HIV, delaying the onset of AIDS, or treating AIDS.

Novel intermediates useful in the preparation of the final compounds and novel synthetic methods are also part of the instant invention.

Pharmaceutical compositions of one or more of the compounds of Formula I use a further part of this invention.

DETAILED DESCRIPTION OF THE INVENTION

The instant invention is a compound of Formula I

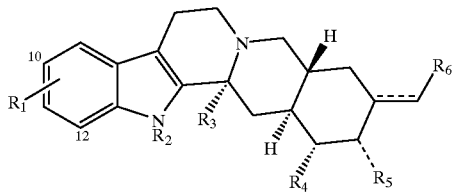

or a pharmaceutically acceptable salt thereof wherein:
the --- means a double bond is possible;
$R_1$ is hydrogen, lower alkyl, lower alkenyl, alkoxy, hydroxy, halogen, $CH_2OH$, trifluoromethyl, nitro, cyano, amino, substituted amino, or $(CH_2)_m$—COOR wherein m is an integer of from 0 to 2 and R is alkyl or hydrogen;
$R_2$ is hydrogen or lower alkyl;
$R_3$ is lower alkyl, lower alkenyl, benzyl, or aryl;
$R_4$ is hydrogen, lower alkyl, —COOR, —CONHR wherein R is hydrogen, alkyl, or aryl;
$R_5$ is hydroxyl, amino, or carbonyl; and
$R_6$ is phenyl, substituted phenyl, naphthyl, or a heterocycle with the proviso that $R_3$ is not methyl when $R_4$ is hydrogen, $R_5$ is hydroxy, and $R_6$ is phenyl.

The invention is also methods of treatment comprising administering a compound of Formula II or the compound [2R[2α(E),4aα, 13bβ, 14aβ]]3-Benzylidene-13b-methyl-1,2,3,4,4a,5,7,9,13,13b,14,14a-dodecahydroindolo[2',3':3,4]pyrido[1,2-b]isoquinolin-2-ol. These methods are: atherosclerosis, restenosis, immune disorders, transplant rejection, virus, preventing infection by HIV, treating infection by HIV, delaying the onset of AIDS, and treating AIDS. The compounds are also useful for modulating the CCR-5 receptor activity.

In the compounds of Formula I and II, the term lower alkyl means a straight or branched alkyl of from 1 to 4 carbon atoms and includes, for example, methyl, ethyl, n-propyl, isopropyl, n-butyl, sec-butyl, isobutyl, or tert-butyl.

The lower alkenyl means a straight or branched carbon chain of from 2 to 6 carbons with one or more double bonds.

The alkoxy is o-alkyl as defined above for alkyl.

Halogen is fluorine, chlorine, bromine, or iodine.

Amino is optionally substituted by one or more selected from methyl, ethyl, n-propyl, or i-propyl.

Phenyl may optionally be substituted with from 1 to 3 substituents selected from lower alkyl, alkoxy, hydroxy, halogen, trifluoromethyl, nitro, cyano, amino, substituted amino, $COOR_7$, $CONR_8R_9$, or phenyl wherein $R_7$, $R_8$, and $R_9$ are each independently selected from hydrogen, alkyl, or aryl.

Preferably, heterocycle is 5- or 6-membered mono- or bicyclic ring structures which may contain one or more heteroatom such as N or O; examples of heterocycle are pyrrole, furan, thiophene, benzofuran, benzothiophene, pyridine, pyrimidine, pyridazine, pyrazole, oxazole, indole, N-alkylindole, quinoline, quinazoline, quinazolinone and the like. Substituents can be hydrogen, alkyl of from 1 to 4 carbon atoms; cycloalkyl of from 5 to 7 carbon atoms, alkoxy, hydroxy, —CN, halogen, trifluoromethyl, nitro, amino, or substituted amino.

Aryl is unsubstituted or substituted phenyl or naphthyl.

The term "mammal" includes animals and humans.

Some of the compounds of Formula I and Formula II are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, 2-phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," *J. Pharma. Sci.*, 1977;66:1).

The acid addition salts of said basic compounds can be prepared by contacting the free base form with a sufficient amount of the desired acid to produce the salt in the conventional manner. The free base form may be regenerated by contacting the salt form with a base and isolating the free base in the conventional manner. The free base forms can differ from their respective salt forms somewhat in certain physical properties such as solubility in polar solvents.

Pharmaceutically acceptable base addition salts can be formed with metals or amines, such as alkali and alkaline earth metals or organic amines. Examples of such metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see Berge, Supra, 1977).

The base addition salts of said acidic compounds can be prepared by contacting the free acid form with a sufficient amount of the desired base to produce the salt in the conventional manner. The free acid form may be regenerated by contacting the salt form with an acid and isolating the free acid in the conventional manner. The free acid forms can differ from their respective salt forms somewhat in certain physical properties such as solubility in polar solvents.

Certain of the compounds of the present invention can exist in unsolvated forms as well as solvated forms, including hydrated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds are valuable agents for the treatment of inflammatory diseases or conditions, atherosclerosis, restenosis, and autoimmune disorders such as arthritis and transplant rejection.

In a preferred embodiment, the disease or condition is one which is associated with lymphocyte and/or monocyte infiltration of tissues (including recruitment and/or accumulation in tissues), such as arthritis (e.g., rheumatoid arthritis), inflammatory bowel diseases (e.g., Crohn's disease, ulcerative colitis), multiple sclerosis, idiopathic pulmonary fibrosis, and graft rejection (e.g., in transplantation), including allograft rejection or graft-versus-host disease. In addition, diseases characterized by basophil activation and/or eosinophil recruitment, including allergic hypersensitivity disorders such as asthma and allergic rhinitis can be treated according to the present invention.

Other diseases that may be treated with the compounds of Formula 1 are: psoriasis, chronic contact dermatitis, sarcoidosis, dermatomyositis, skin phemphigoid and related diseases (e.g., *pemphigus vulgaris, p. foliacious, p. erythematosus*), glomerulonephritides, vasculitides (e.g., necrotizing, cutaneous, and hypersensitivity vasculitis), hepatitis, diabetes, systemic lupus erythematosus and myasthenia gravis.

In addition to psoriasis, other inflammatory dermatoses such as dermatitis, eczema, atopic dermatitis, allergic contact dermatitis, urticaria and reperfusion injury can also be treated.

MCP-1 BINDING ASSAY

Membranes used in the MCP-1 binding assay were prepared from THP-1 cells (human monocytic cell line source-American Type Culture Collection, Tumor Immunology Bank #202, Rockville, Md., accession No. ATCC TIB 202). Cells were harvested by centrifugation and washed twice in ice-cold PBS (phosphate-buffered saline) and the cell pellet was frozen at −80° C. in some cases. Cells were resuspended in ice-cold lysis buffer 5 mM HEPES (2-(4N-[2-hydroxyethyl]piperazin-1-yl)-N'-(2-ethanesulfonic acid), pH 7.5, 2 mM EDTA (ethylenediaminetetraacetic acid), 5 $\mu$g/mL each leupeptin, aprotinin, chymostatin (protease inhibitors), and 100 $\mu$g/mL PMSF (phenylmethane sulfonyl fluoride—also a protease inhibitor)) at a concentration of $5 \times 10^7$ cells/mL. The cell suspension was dounced 10 to 15 times using the B pestle (small pestle of tissue grinder—clearance is 0.07 mm; source—Fisher Scientific) on ice. Nuclei and debris were removed by centrifugation at 500 to 1000×g for 10 minutes at 4° C. The supernatant was transferred to a fresh tube and centrifuged at 25,000×g for 30 minutes at 4° C. The supernatant was aspirated, and the pellet was resuspended in freezing buffer (10 mM HEPES, pH 7.5, 300 mM sucrose, 1 $\mu$g/mL each leupeptin, aprotinin, chymostatin, and 10 $\mu$g/mL PMSF) using a mini-homogenizer until all clumps were resolved. Membranes were aliquoted and frozen at minus 70° C. to 85° C. until needed. Typical binding assays used 10 to 20 $\mu$g/well of total membrane protein as determined with a standard protein assay (e.g. Bradford protein assay, BioRad, Richmond, Calif.).

For binding, 10 to 20 $\mu$g of total membrane protein were included in the binding reaction along with 0.2 nM $I^{125}$-labeled MCP-1 (Amersham, Arlington Heights, Ill.) with or without unlabeled competitor MCP-1 (Peprotech, Rocky Hill, N.J.) (at 500 nM). Binding reactions were performed in a final volume of 100 $\mu$L in a binding buffer containing 10 mM HEPES, pH 7.2, 1 mM $CaCl_2$, 5 mM $MgCl_2$, 0.5% BSA (bovine serum albumin). After 30 to 60 minutes at room temperature, the binding reactions were filtered through GF/C filters (Whatman glass fiber filters, Type C) or GF/B unifilter plates (Packard) which had been pre-soaked with 0.3% polyethyleneimine and washed twice with binding buffer containing 0.5 M NaCl. Filters were dried and counted in a Beta-Plate scintillation counter using standard scintillation fluid. Final concentration of compound in the binding assay ranged from 0.05 to 100 TM. Compounds were dissolved in DMSO (dimethyl sulfoxide). Final concentrations of DMSO in the binding were kept constant at 0.5%.

$IC_{50}$s were calculated using a non-linear 3-parameter logistic curve fit. $IC_{50}$ means the concentration at which 50% inhibition is achieved. Negative controls contained the same amount of DMSO vehicle as used in wells containing compound. Positive control contained 250 to 500 nM cold competitor MCP-1 in DMSO vehicle. Non-specific binding (the level of bound $^{125}$I-labeled MCP-1 in the presence of 250 to 500 TM unlabeled MCP-1) was subtracted from all data prior to analysis.

The compounds of the invention have $IC_{50}$s between about 1.0 to 50 micromolar at CCR-2 receptor.

CCR-5 Receptor Binding Assay

The $^{125}$I-gp120/sCD4/CCR-5 binding assay was carried out similarly as described in Wu et al., *Nature*, 1996;384: 179–183. Briefly, the envelope gp120 protein derived from HIV-1 JR-FL (Trkola et al., *Nature*, 1996;384:184–186), a M-tropic strain, was iodinated using solid phase lactoperoxidase to a specific activity of 20 $\mu$Ci/$\mu$g. For each binding reaction (in a final volume of 100 $\mu$L binding buffer [50 mM HEPES, pH 7.5, 1 mM $CaCl_2$, 5 mM $MgCl_2$, and 0.5% BSA]), 25 $\mu$L (2.5 $\mu$g) of membranes prepared from CCR-5/L 1.2 cells were mixed with 25 $\mu$L (3 nM) sCD4, followed by 25 $\mu$L (0.1 nM) radio-labeled gp120 in the presence or absence of 25 $\mu$L compound dissolved in DMSO (final concentration of DMSO 0.5%). The reactions were incubated at room temperature for 45 to 60 minutes and stopped by transferring the mixture to GFB filter plates, which were then washed 3 to 4 times with binding buffer containing 0.5 M NaCl. The plates were dried and MicroScint scintillation fluid was added before counting.

The compounds of the invention have $IC_{50}$s between about 0.2 to 50 micromolar at the CCR-5 receptor.

The compounds of the present invention can be prepared and administered in a wide variety of routes of administration such as parenteral, oral, topical, rectal, inhalation and the like. Formulations will vary according to the route of administration selected. Examples are oral and parenteral dosage forms. Thus, the compounds of the present invention can be administered by injection, that is, intravenously, intramuscularly, intra-cutaneously, subcutaneously, intraduodenally, or intra-peritoneally. Also, the compounds of the present invention can be administered by inhalation, for example, intranasally. Additionally, the compounds of the present invention can be administered transdermally. The following dosage forms may comprise as the active component, a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier can be a finely divided solid which is in a mixture with the finely divided active component.

In tablets, the active component can be mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories a low melting wax, such as a mixture of fatty acid glycerides or cocoa butter, is first melted and the active component can be dispersed homogeneously therein, as by stirring. The molten homogenous mixture can be then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in a pharmaceutically acceptable carrier, such as, aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water or another suitable carrier with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted for example from about 0.1 mg to 200 mg, preferably about 0.5 mg to 100 mg according to the particular application and the potency of the active component. The composition can, if desired, also contain other compatible therapeutic agents.

In therapeutic use as agents for the treatment of inflammatory diseases, inflammatory diseases, atherosclerosis, restenosis, and immune disorders such as arthritis and transplant rejection, the compounds utilized in the pharmaceutical methods of this invention can be administered at an initial dosage of about 0.01 mg to about 200 mg/kg daily. A daily dose range of about 0.01 mg to about 50 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

General Preparative Methods for Compounds of the Invention

In the IUPAC systematic nomenclature, these compounds are named as derivatives of indolo[2',3':3,4]pyrido[1,2-b]isoquinoline. In this system, the 13b-,2-, and 3-substituent positions correspond to the 3-, 17-, and 18-positions, respectively, in the older nomenclature based on the natural product yohimbine.

Imminium salts of indolo[2',3':3,4]pyrido[1,2-b]isoquinolines 1 are reacted with an alkyl or aryl lithium reagent or an alkyl or aryl Grignard reagent to yield the 13b-alkyl or aryl derivatives 2 (Scheme 1 below). The reaction may be carried out in tetrahydrofuran or diethyl ether at 0 to 70 degrees for 1 to 24 hours, following the method of Zinnes H., Comes R. A., and Shavel J., Jr., *J. Org. Chem.*, 1965;30:105. The starting imminium salts 1 are prepared as described in the above reference, or by Godtfredsen W. O. and Vangedal S., *Acta Chem. Scand.*, 1956;10:1414. Compounds of type 2 in which $R_3$ is hydrogen are also prepared from the natural product yohimbine as described by Aube J. and Ghosh S., *Advances in Natural Product Synthesis*, 1996;3:99, and Baxter E. W. and Mariano P. S., in *Alkaloids: Chemical and Biological Perspectives*; Pelletier S. W., Ed., Springer-Verlag: New York, 1992;8:197–319. Alternatively, the imminium salts 1 are reacted with allyltributyl tin or tetraallyl tin to produce the 13b-allyl derivatives 3. The reaction may be run in an alcohol such as methanol, ethanol, or 2-methoxyethanol, or a mixed solvent system consisting of an alcohol and chloroform or dichloromethane at 40 to 125 degrees for 1 to 24 hours. The 13b-allyl adducts 3 thus prepared may be subjected to catalytic hydrogenation to obtain the corresponding 13b-propyl analogs 4.

The compounds of type 2 are oxidized at the 2-carbinol substituent to yield the ketone derivatives 5 (Scheme 2 below). The oxidation may be performed by the Oppenauer method utilizing an aluminum alkoxide reagent (Zinnes H., Comes R. A., and Shavel J., Jr., reference cited above), or with tetrapropylammonium perruthenate (TPAP; Ley S. V., Norman J., Griffith W. P., and Marsden S. P., *Synthesis*, 1994:639), or with dimethyl sulfoxide and oxalyl chloride (Swern oxidation; Tidwell T. T., *Organic Reactions*, 1990;39:297). Condensation of the ketones 5 with an aromatic aldehyde 6 in methanol or ethanol at 50 to 80 degrees for 2 to 24 hours in the presence of aqueous sodium hydroxide or potassium hydroxide yields the benzylidene ketones 7 when $R_6$ is phenyl or substituted phenyl. The benzylidene moiety may be reduced to a benzyl substituent by standard catalytic hydrogenation methods Reduction of the ketones 7 with sodium borohydride or potassium borohydride in methanol, ethanol, or tetrahydrofuran at 25 to 80 degrees for 2 to 24 hours gives the carbinols 8 (Shavel J., Jr., Bobowski G., and von Strandtmann M., U.S. Pat. No. 3,139,428).

The benzene ring of the indole portion of these compounds may be subjected to standard aromatic substitution reactions, such as bromination and nitration, in order to prepare compounds 10–15 (Schemes 3 and 4). In addition, the ketones 7 may be converted to oximes 16 and the oximes reduced to obtain amines 17 (Scheme 5).

Scheme 1
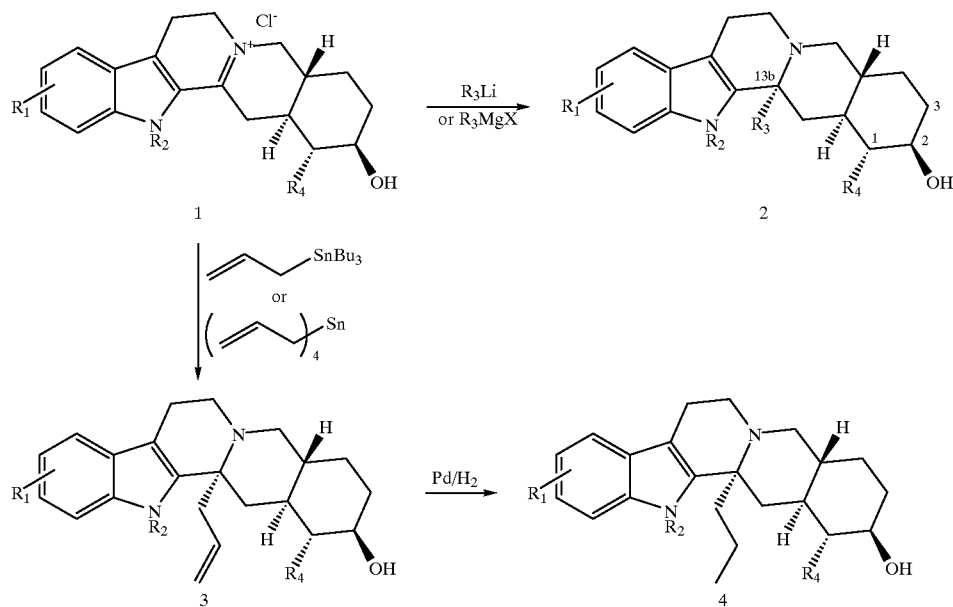
Scheme 2
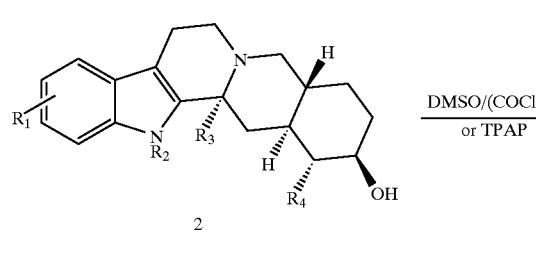
Scheme 3
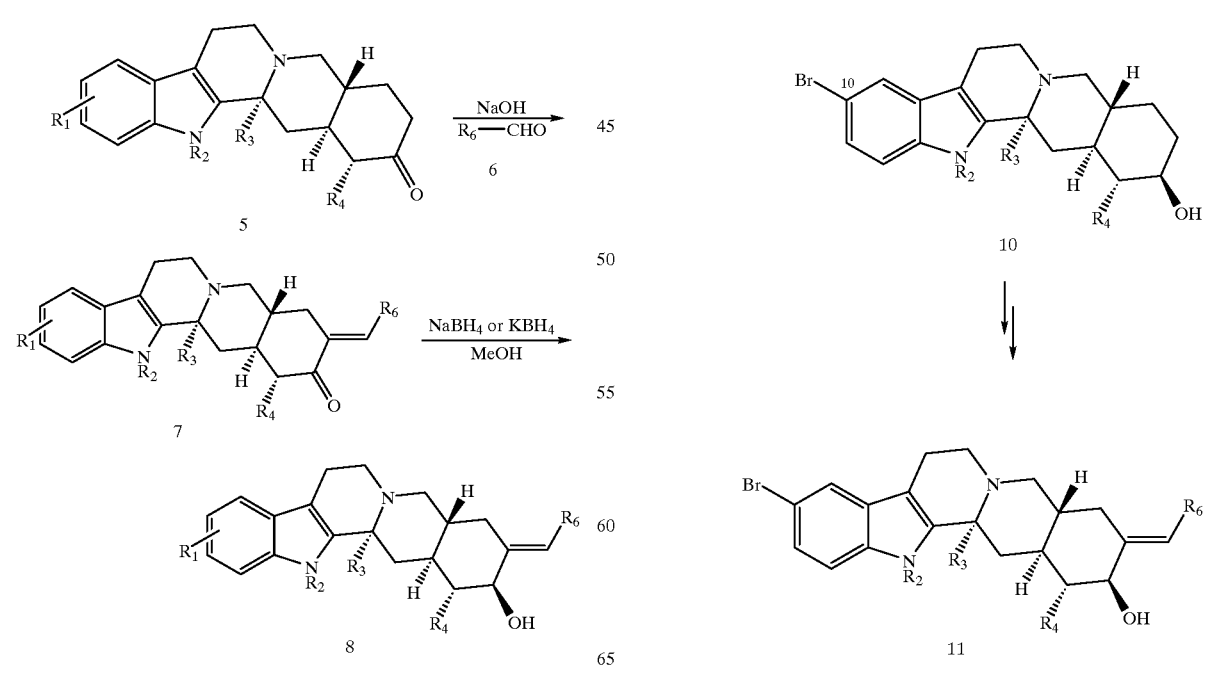

Scheme 4

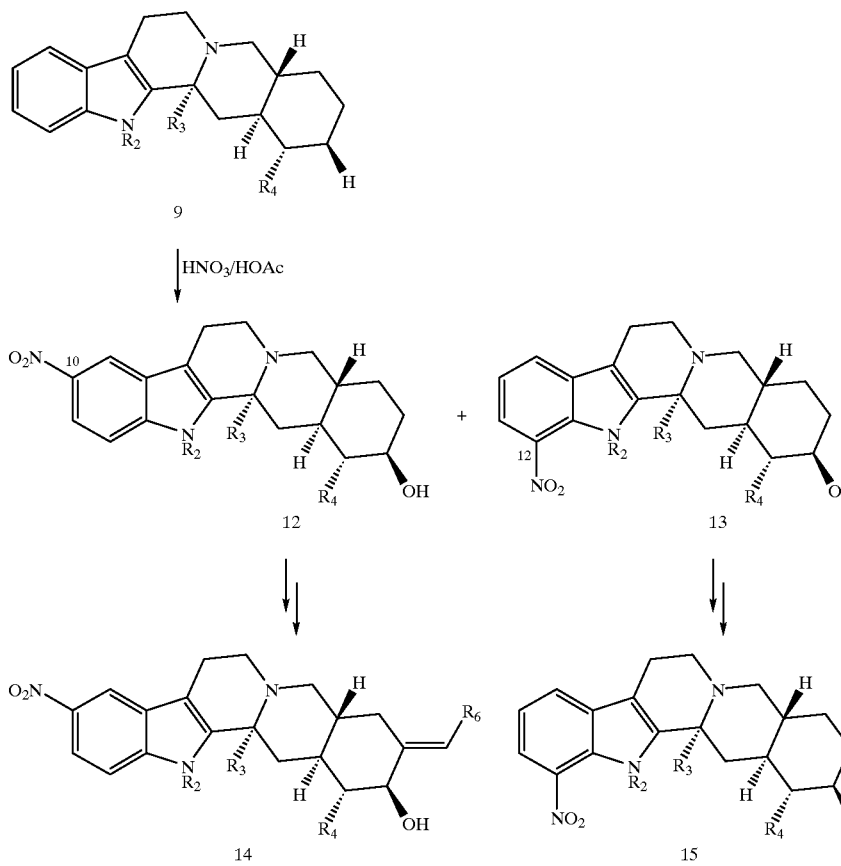

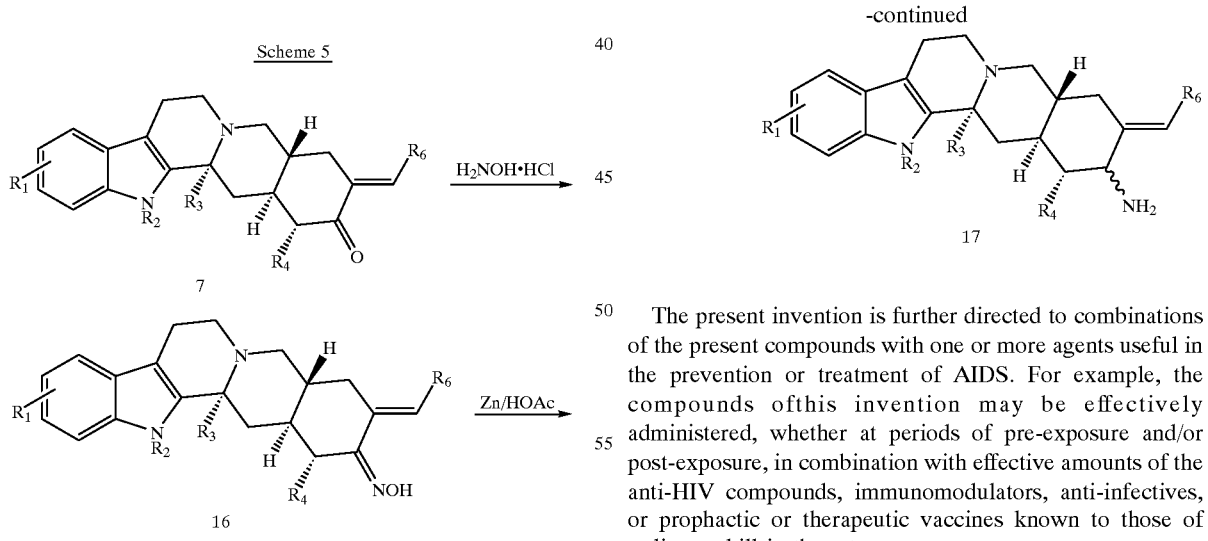

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the anti-HIV compounds, immunomodulators, anti-infectives, or prophactic or therapeutic vaccines known to those of ordinary skill in the art.

ANTIVIRALS

| Drug Name | Manufacturer | Indication |
|---|---|---|
| 097 | Hoechst/Bayer | HIV infection, AIDS, ARC (non-nucleoside reverse transcriptase (RT) inhibitor) |
| GW141 W94/ VX478 Amprenavir | Glaxo Wellcome | HIV infection, AIDS, ARC (protease inhibitor) |
| GW1592U89 Abacavir | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in Combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination |
| Alferon Interferon | Interferon Sciences | Kaposi's sarcoma, HIV in combination |
| Ansamycin LM 427 | Adria Laboratories (Dublin, OH) Erbamont Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infections, AIDS, ARC |
| beta-fluoro-ddA | Nat'l Cancer Institute | AIDS-associated diseases |
| BMS-232623 (CGP-73547) | Bristol-Myers Squibb/Novartis | HIV infection, AIDS, ARC (protease inhibitor) |
| BMS-234475 (CGP-61755) | Bristol-Myers Squibb/Novartis | HIV infection, AIDS, ARC (protease inhibitor) |
| (-)6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Combivir AZT + 3TC | Glaxo Wellcome | HIV infection, AIDS, ARC |
| Curdlan sulfate | AJI Pharma USA | HIV infection |
| Cytomegalovirus immune globin | MedImmune | CMV retinitis |
| Cytovene Ganciclovir | Syntex/Roche | Sight threatening CMV, peripheral CMV, retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| HIVID (ddc) Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | Triangle Pharmaceutical | HIV infection, AIDS, ARC (protease inhibitor) |
| Efavirenz (DMP 266) | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | Herpes zoster, herpes simplex |
| Foscavir/Foscarnet | Astra | CMV, HSV 1-2 |
| FTC | Triangle Pharmaceutical | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alpha-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| JE 2147 (KNI-764) | Japan Energy/ Agouron PI | HIV infection, AIDS, ARC (reverse transcriptase inhibitor); also with AZT |
| Protease inhibitor | | |
| KNI-272 | Nat'l Cancer Institute | HIV-associated diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection-HBV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| PNU-140690 | Pharmacia Upjohn | HIV infection, AIDS, ARC (protease inhibitor) |
| Probucol | Vyrex | HIV infection, AIDS |
| RBD-CD4 | Sheffield Med. Tech (Houston, TX) | HIV infection, AIDS, ARC |
| Ritonavir | Abbott | HIV infection, AIDS, ARC (protease inhibitor) |
| S-1153 | Agouron/Shionogi | NnRTI |
| Saquinavir | Hoffmann-La Roche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Gential HSV & CMV infections |
| Virazole Ribavirin | Viratek/ICN (Costa Mesa, CA) | Asymptomatic HIV positive, LAS, ARC |
| Zidovudine; AZT | Glaxo Wellcome | HIV infection, AIDS, ARC, Kaposi's sarcoma, in combination with other therapies |

| IMMUNO-MODULATORS | | |
|---|---|---|
| Drug Name | Manufacturer | Indication |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV core Particle Immunostimulant | Rorer | Seropositive HIV |
| IL-2 Interleukin-2 | Cetus | AIDS, in combination w/AZT |
| IL-2 Interleukin-2 | Hoffman-La roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK & F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

| ANTI-INFECTIVES | | |
|---|---|---|
| Drug Name | Manufacturer | Indication |
| Clindamycen with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | Cryptosporidial diarrhea |
| Intraconazole-R51211 | Janssen Pharm. | Histoplasmosis; cryptococcal meningitis |
| Trimetrexate | Warner-Lambert | PCP |

| OTHER | | |
|---|---|---|
| Drug Name | Manufacturer | Indication |
| Daunorubicin | NeXstar, Sequus | Karposi's sarcoma |
| Recombinant Human Erythropoietin | Ortho Pharm. Corp. | Severe anemia associated with AZT therapy |
| Recombinant Human Growth Hormone | Serono | AIDS-related wasting, cachexia |
| Megestrol Acetate | Bristol-Myers Squibb | Treatment of anorexia associated w/AIDS |
| Testosterone | Alza, Smith Kline | AIDS-related wasting |
| Total Enteral Nutrition | Norwich Eaton Pharmaceuticals | Diarrhea and malabsorption related to AIDS |

It will be understood that the scope of combinations of the compounds of this invention with AIDS antivirals, immunomodulators, anti-infectives or vaccines is not limited to the list in the above table, but includes in principle any combination with any pharmaceutical composition useful for the treatment of AIDS.

The following examples are illustrative of the instant invention. They do not limit the scope of the invention.

EXAMPLE 1

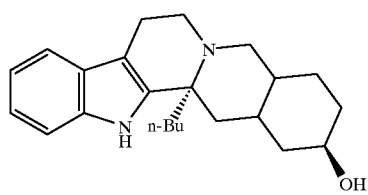

[2R-(2α,4aα, 13β,14aβ)]-13b-Butyl-1,2,3,4,4a,5,7,8,13, 13b,14,14a-dodecahydro-indolo[2',3':3,4]pyrido[1,2-b] isoquinolin-2-ol A suspension of [2R-(2α,4aα,14aβ)]-2-hydroxy-2,3,4,4a, 5,7,8,13,14,14a-decahydro-1H-indolo[2',3':3,4]pyrido[1,2-b]isoquinol in-6-ylium chloride (10.6 g, 32.0 mmol; Zinnes H., Comes R. A., and Shavel J., Jr., *J. Org. Chem.*, 1965;30:105) in 600 mL of diethyl ether was cooled in an ice bath while a solution of n-butyl lithium (100 mL, 160 mmol of 1.6 M in hexane) was added dropwise. The mixture was stirred at room temperature for 18 hours, then at reflux for 6 hours. The mixture was again cooled in ice and treated dropwise with 200 mL of saturated aqueous ammonium chloride solution. The mixture was filtered, and the filtrate layers were separated. The aqueous layer was extracted with ethyl acetate, and the extracts were combined with the original organic layer. The insoluble material was digested several times with warm ethyl acetate. The mixture was filtered, and the filtrate was added to the original ethyl acetate extracts. The combined organic layers were washed with brine, dried (Na$_2$SO$_4$), and evaporated. The residue was purified by flash chromatography (2% triethylamine in ethyl acetate) to yield 1.8 g (16%) of product. A sample recrystallized twice from aqueous 2-propanol had mp 235° C. dec.;

$^1$H NMR (DMSO-d$_6$)δ 0.63–0.79 (m, 4H), 0.82–1.15 (m, 2H), 1.17–1.28 (m, 5H), 1.35–1.52 (m, 3H), 1.61–1.72 (m, 3H), 1.87 (m, 1H), 2.13 (m, 1H), 2.55–2.76 (m, 4H), 2.87 (m, 1H), 3.09 (m, 1H), 3.46 (m, 1H), 4.49 (d, J=4.6 Hz, 1H), 6.89–7.00, (m, 2H), 7.24 (d, J=8.0 Hz, 1H), 7.32 (d, J=7.5 Hz, 1H), 10.59 (s, 1H); MS (APCI$^+$), m/z 353 (MH$^+$).

EXAMPLE 2

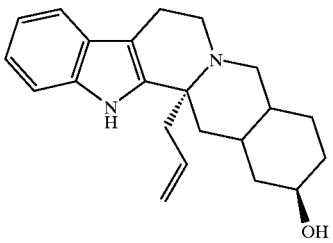

[2R-(2α,4aα,13β,14aβ)]-13b-Allyl-1,2,3,4,4a,5,7,8,13,13b,14,14a-dodecahydro-indolo[2',3':3,4]pyrido[1,2-b]isoquinolin-2-ol A suspension of [2R-(2α,4aα,14aβ)]-2-hydroxy-2,3,4,4a,5,7,8,13,14,14a-decahydro-1H-indolo[2',3':3,4]pyrido[1,2-b]isoquinolin-6-ylium chloride (11.2 g, 33.9 mmol) and tetraallyl tin (10.5 mL, 12.4 g, 43.7 mmol) in 100 mL of 2-methoxyethanol was stirred at reflux for 4 hours. The cooled reaction mixture was added to 1.0 L of 5% aqueous sodium bicarbonate solution and 1.0 L of ethyl acetate. The mixture was filtered, and the filtrate layers were separated. The aqueous layer was extracted with fresh ethyl acetate, and the extracts were combined with the original organic layer. The original insoluble material was digested several times with warm ethyl acetate. The mixture was filtered, and the filtrate was added to the original ethyl acetate extracts. The combined organic layers were washed several times with brine, dried (Na$_2$SO$_4$), and evaporated. The residue was purified by flash chromatography (0.75% triethylamine in ethyl acetate) to yield 6.6 g (58% of product. A sample recrystallized from aqueous 2-propanol had mp 228–230° C.;

$^1$H NMR (DMSO-d$_6$) δ 0.87–1.27 (m, 4H), 1.35–1.51 (m, 3H), 1.68 (m, 1H), 1.78–1.93 (m, 2H), 2.52–2.73 (m, 5H), 2.81–3.07 (m, 3H), 3.47 (m, 1H), 4.51 (d, J=4.3 Hz, 1H), 4.81 (dd, J=2.2, 8.2 Hz, 1H), 4.92 (dd, J=2.2, 15.2 Hz, 1H), 5.52 (m, 1H), 6.89–7.01 (m, 2H), 7.25 (d, J=8.0 Hz, 1H), 7.33 (d, J=7.7 Hz, 1H), 10.6 (s, 1H); MS (APCI$^+$), m/z 337 (MH$^+$).

EXAMPLE 3

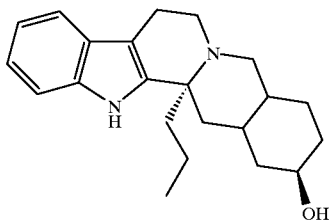

[2R-(2α,4aα,13β,14aβ)]-13b-Propyl-1,2,3,4,4a,5,7,8,13,13b,14,14a-dodecahydro-indolo[2',3':3,4]pyrido[1,2-b]isoquinolin-2-ol A solution of [2R-(2α,4aα,13β,14aβ)]-13b-allyl-1,2,3,4,4a,5,7,8,13,13b,14,14a-dodecahydro-indolo[2',3':3,4]pyrido[1,2-b]-isoquinolin-2-ol (5.3 g, 15.8 mmol) in 100 mL of 50% tetrahydrofiuran/methanol was hydrogenated over 0.5 g of 10% palladium on carbon catalyst. The catalyst was filtered, and the filtrate was evaporated to yield 5.1 g (96%) of the product. A sample purified by flash chromatography (10% methanol in dichloromethane) and recrystallized from ethyl acetate/hexane had mp 195° C. dec.;

$^1$H NMR (DMSO-d$_6$) δ 0.75–0.76 (m, 4H), 0.83–1.06 (m, 2H), 1.08–1.32 (m, 3H), 1.33–1.52 (m, 3H), 1.58–1.77 (m, 3H), 1.87 (m, 1H), 2.07 (m, 1H), 2.53–2.75 (m, 4H), 2.88 (m, 1H), 3.09 (m, 1H), 3.45 (m, 1H), 4.49 (d, J=4.6 Hz, 1H), 6.89–7.00 (m, 2H), 7.24 (d, J=8.0 Hz, 1H), 7.32 (d, J=7.7 Hz, 1H), 10.59 (s, 1H); MS (APCI$^+$), m/z 339 (MH$^+$).

EXAMPLE 4

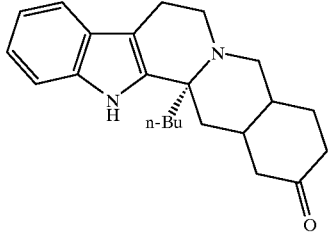

[2R-(2α,4aα, 13β,14aβ)]-13b-Butyl-3,4,4a,5,7,8,13,13b,14,14a-decahydro-1H-indolo[2',3':3,4]pyrido[1,2-b]isoquinolin-2-one A solution of oxalyl chloride (0.52 mL, 0.76 g, 6.0 mmol) in 15 mL of dichloromethane was cooled to −78° C. while a solution of dimethyl sulfoxide (1.0 mL, 1.1 g, 14.1 mmol) in 5.0 mL of dichloromethane was added dropwise. The mixture was stirred for 15 minutes, and a solution of [2R-(2α,4aα, 13β,14aβ)]-13b-butyl-1,2,3,4,4a,5,7,8,13,13b,14,14a-dodecahydro-indolo[2',3':3,4]pyrido[1,2-b]isoquinolin-2-ol (1.8 g, 5.1 mmol) in 25 mL of tetrahydrofuran was added dropwise. The mixture was stirred for 30 minutes, and N,N'-diisopropylethylamine (4.5 mL, 3.3 g, 25.8 mmol) was added dropwise. The cooling bath was removed, and the mixture was stirred for 16 hours. The reaction mixture was added to 400 g of ice and water and extracted with ethyl acetate. The combined organic layers were washed with brine, dried (Na$_2$SO$_4$), and evaporated. The residue was purified by flash chromatography (50:50:1 ethyl acetate/hexane/triethylamine) to yield 1.4 g (76%) of product of mp 235° C. dec.;

$^1$H NMR (DMSO-d$_6$) δ 0.63–0.77 (m, 4H), 1.09–1.41 (m, 4H), 1.55–1.87 (m, 6H), 5 2.01–2.29 (m, 4H), 2.35–2.47 (m, 1H), 2.57–2.72 (m, 2H), 2.73–2.82 (m, 2H), 2.90–2.97 (m,

1H), 3.12–3.21 (m, 1H), 6.90–7.02 (m, 2H), 7.25 (d, J=8.0 Hz, 1H), 7.34 (d, J=7.7 Hz, 1H), 10.62 (s, 1H); MS (APCI⁺), m/z 351 (MH⁺).

EXAMPLE 5

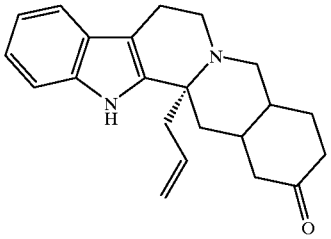

[2R-(2α,4aα,13β,14aβ)]-13b-Allyl-3,4,4a,5,7,8,13,13b,14,14a-decahydro-1H-indolo[2',3':3,4]pyrido[1,2-b]isoquinolin-2-one Prepared in 76% yield from [2R-(2α,4aα,13β,14aβ)]-13b-allyl-1,2,3,4,4a,5,7,8,13,13b,14,14a-dodecahydro-indolo[2',3':3,4]pyrido[1,2-b]-isoquinolin-2-ol by the procedure described in Example 4. Recrystallization from ethyl acetate/hexane gave product of mp 220–223° C.;

$^1$H NMR (DMSO-d$_6$) δ 1.30–1.38 (m., 1H), 1.48 (t, J=13.0 Hz, 1H), 1.75–1.81 (m, 4H), 1.98–2.21 (m, 3H), 2.33–3.08 (m, 9H), 4.75 (dd, J=2.2, 10.0 Hz, 1H), 4.87 (d, J=17.3 Hz, 1H), 5.45 (m, 1H), 6.85–6.96 (m, 2H), 7.20 (d, J=7.8 Hz, 1H), 7.29 (d, J=7.8 Hz, 1H), 10.59 (s, 1H); MS (APCI⁺), m/z 335 (MH⁺).

EXAMPLE 6

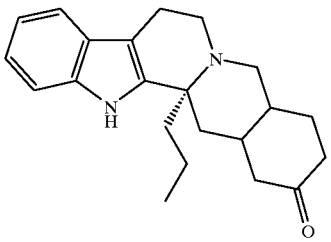

[2R-(2α,4aα,13β,14aβ)]-13b-Propyl-3,4,4a,5,7,8,13,13b,14,14a-decahydro-1H-indolo[2',3':3,4]pyrido[1,2-b]isoquinolin-2-one Prepared in 75% yield from [2R-(2α,4aα,13β,14aβ)]-13b-propyl-1,2,3,4,4a,5,7,8,13,13b,14,14a-dodecahydro-indolo[240,3':3,4]pyrido[1,2-b]-isoquinolin-2-ol by the procedure described in Example 4. Recrystallization from ethyl acetate/hexane gave product of mp 255° C. dec.;

$^1$H NMR (DMSO-d$_6$) δ 0.75–0.79 (m, 4H), 1.17–1.39 (m, 2H), 1.56–1.68 (m, 2H), 1.74–1.81 (m, 4H), 2.03–2.26 (m, 4H), 2.38–3.19 (m, 7H), 6.90–7.01 (m, 2H), 7.25 (d, J=7.7 Hz, 1H), 7.33 (d, J=7.7 Hz, 1H), 10.62 (s, 1H); MS (APCI⁺), m/z 337 (MH⁺).

EXAMPLE 7

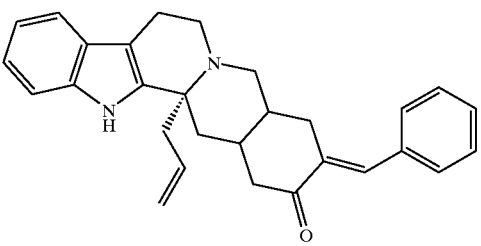

[4aS-(2E,4aα,13β,14aβ)]-13b-Allyl-3-benzylidene-3,4,4a,5,7,8,13,13b,14,14a-decahydro-1H-indolo[2',3':3,4]pyrido[1,2-b]isoquinolin-2-one A solution of [2R-(2α,4aα,13β,14aβ)]-13b-allyl-3,4,4α,5,7,8,13,13b,14,14a-decahydro-1H-indolo[2',3':3,4]pyrido[1,2-b]-isoquinolin-2-one (0.26 g, 0.78 mmol) in 7.0 mL of methanol and 0.32 mL (0.80 mmol) of 10% aqueous sodium hydroxide was heated to reflux. A solution of benzaldehyde (0.21 mL, 0.22 g, 2.1 mmol) in 3.0 mL of methanol was added dropwise, and heating was continued for 4 hours. The cooled reaction mixture was evaporated, and the residue was partitioned between ethyl acetate and brine. The organic layer was dried (Na$_2$SO$_4$) and evaporated. Purification of the residue by flash chromatography (25:75:1 ethyl acetate/hexane/triethylamine) gave 0.27 g (82%) of the product as a foam;

$^1$HNMR (DMSO-d$_6$) δ 6 0.78–0.98 (m, 1H), 1.14 (s, 2H), 1.50 (t, J=12.1 Hz, 1H), 1.67–1.81 (m, 1H), 1.87–1.95 (m, 1H), 2.08–2.24 (m, 2H), 2.38–2.72 (m, 3H), 2.77–3.21 (m, 5H), 4.83 (d, J=10.3 Hz, 1H), 4.97 (d, J=17.1 Hz, 1H), 5.45–5.60 (m, 1H), 6.87–7.03 (m, 2H), 7.21–7.53 (m, 8H), 10.67 (s, 1H); MS (APCI⁺), m/z 423 (MH⁺).

EXAMPLE 8

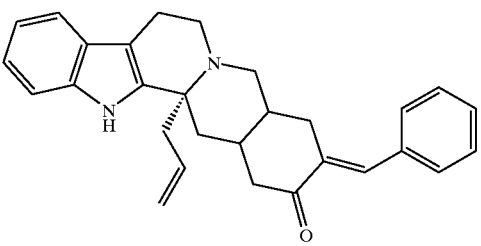

[4aS-(2E,4aα,13β,14aβ)]-3-Benzylidine-13b-propyl-3,4,4a,5,7,8,13,13b,14,14a-decahydro-1H-indolo[2',3':3,4]pyrido[1,2-b]isoquinolin-2-one Prepared in 71% yield from [2R-(2α,4aα,13β,14aβ)]-13b-propyl-3,4,4a,5,7,8,13,13b,14,14a-decahydro-1H-indolo[2',3':3,4]pyrido[1,2-b]-isoquinolin-2-one by the procedure described in Example 7. The product was obtained as a foam;

$^1$H NMR (DMSO-d$_6$) δ 0.71–0.88 (m, 4H), 1.21–1.36 (m, 1H), 1.58 (t, J=12.3 Hz, 1H), 1.63–1.79 (m, 2H), 1.83 (m, 1H), 2.02–2.23 (m, 3H), 2.30–2.70 (m, 4H), 2.78–2.95 (m, 4H), 3.05–3.19 (m, 1H), 6.89–7.01 (m, 2H), 7.11–7.52 (m, 8H), 10.64 (s, 1H); MS (APCI⁺), m/z 425 (MH⁺).

EXAMPLE 9

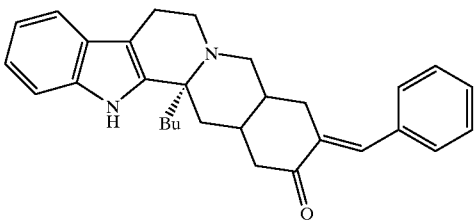

[4aS-(2E,4aα,13β,14aβ)]-3-Benzylidine-13b-butyl-3,4,4a,5,7,8,13,13b,14,14a-decahydro-1H-indolo[2',3':3,4]pyrido[1,2-b]isoquinolin-2-one Prepared in 31% yield from [2R-(2α,4aα,13β,14aβ)]-13b-butyl-3,4,4a,5,7,8,13,13b,14,14a-decahydro-1H-indolo[2',3':3,4]pyrido[1,2-b]-isoquinolin-2-one by the procedure described in Example 7. The product was obtained as a foam;

$^1$H NMR (DMSO-d$_6$) δ 0.64–0.82 (m, 4H), 1.12–1.30 (m, 3H), 1.51–1.84 (m, 4H), 2.03–2.28 (m, 3H), 2.32–2.71 (m, 4H), 2.78–2.95 (m, 4H), 3.08–3.18 (m, 1H), 6.89–7.01 (m, 2H), 7.25–7.50 (m, 8H), 10.64 (s, 1H); MS (APCI$^+$), m/z 439 (MH$^+$).

EXAMPLE 10

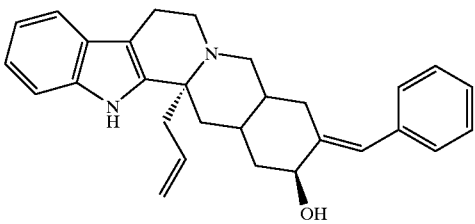

[2S-(2α,4aα,13β,14aβ)]-13b-Allyl-3-benzylidene-1,2,3,4,4a,5,7,8,13,13b,14,14a-dodecahydro-indolo[2',3':3,4]pyrido[1,2-b]isoquinolin-2-ol A solution of [4aS-(2E,4aα,13β,14aβ)]-13b-allyl-3-benzylidene-3,4,4a,5,7,8,13,13b,14,14a-decahydro-1H-indolo[2',3':3,4]pyrido[1,2-b)-isoquinolin-2-one (1.8 g, 4.3 mmol) in 75 mL of methanol was cooled in an ice bath and treated slowly with sodium borohydride (0.73 g, 19.3 mmol). The mixture was stirred at room temperature for 18 hours. The solvent was evaporated, and the residue was partitioned between ethyl acetate and water. The layers were separated, and the aqueous layer was extracted with fresh ethyl acetate. The combined organic layers were washed with brine, dried (Na$_2$SO$_4$), and evaporated. The residue was purified by flash chromatography (33:67:0.5 ethyl acetate/hexane/triethylamine) to yield 1.3 g (72%) of product. A sample recrystallized from ethyl acetate/hexane had mp 211–213° C.;

$^1$H NMR (DMSO-d$_6$) δ 1.09 (q, J=11.5 Hz, 1H), 1.26–1.38 (m, 1H), 1.41 (t, J=12.7 Hz, 1H), 1.64 (t, J=12.9 Hz, 1H), 1.72–1.77 (m, 1H), 1.86–1.92 (m, 2H), 2.55–3.02 (m, 9H), 4.13 (m, 1H), 4.82 (d, J=10.0 Hz, 1H), 4.96 (d, J=17.8 Hz, 1H), 5.10 (d, J=5.1 Hz, 1H), 5.51 (m, 1H), 6.57 (s, 1H), 6.91 (t, J=7.3 Hz, 1H), 6.99 (t, J=7.4 Hz, 1H), 7.18–7.37 (m, 7H), 10.64 (s, 1H); MS (APCI$^+$), m/z 425 (MH$^+$).

EXAMPLE 11

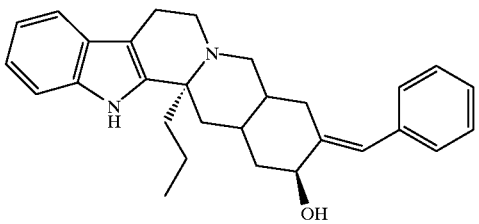

[2S-(2α,4aα,13β,14aβ)]-3-Benzylidine-13b-propyl-1,2,3,4,4a,5,7,8,13,13b,14,14a-dodecahydro-indolo[2',3':3,4]pyrido[1,2-b]-isoquinolin-2-ol Prepared in 80% yield from [4aS-(2E,4aα,13β,14aβ)]-3-benzylidene-13b-propyl-3,4,4a,5,7,8,13,13b,14,14a-decahydro-1H-indolo[2',3':3,4]pyrido[1,2-b]-isoquinolin-2-one by the procedure described in Example 10. A sample recrystallized from ethanol/diethyl ether had mp 224–226° C.;

$^1$H NMR (DMSO-d$_6$) δ 0.76–0.77 (m, 4H), 1.08 (q, J=11.7 Hz, 1H), 1.15–1.35 (m, 2H), 1.46 (t, J=12.5 Hz, 1H), 1.52–1.92 (m, 5H), 2.07–2.20 (m, 1H), 2.52–2.91 (m, 6H), 2.99–3.11 (m, 1H), 4.11 (m, 1H), 5.09 (d, J=4.2 Hz, 1H), 6.56 (s, 1H), 6.91 (t, J=7.4 Hz, 1H), 6.98 (t, J=7.5 Hz, 1H), 7.17–7.36 (m, 7H), 10.62 (s, 1H); MS (APCI$^+$), m/z 427 (MH$^+$).

EXAMPLE 12

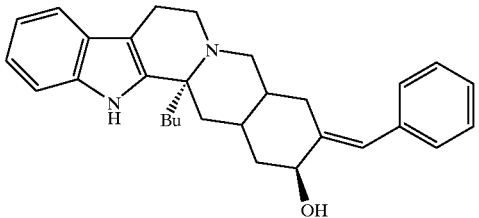

[2S-(2α,4aα,13β,14aβ)]-3-Benzylidine-13b-butyl-1,2,3,4,4a,5,7,8,13,13b,14,14a-dodecahydro-indolo[2',3':3,4]pyrido[1,2-b]-isoquinolin-2-ol Prepared in 68% yield from [4aS-(2E,4aα,13β,14aβ)]-3-benzylidene-13b-butyl-3,4,4a,5,7,8,13,13b,14,14a-decahydro-1H-indolo[2',3':3,4]pyrido[1,2-b]-isoquinolin-2-one by the procedure described in Example 10. A sample recrystallized from aqueous 2-propanol had mp 222–225° C.;

$^1$H NMR (DMSO-d$_6$) δ 0.63–0.81 (m, 4H), 1.02–1.35 (m, 5H), 1.43–1.79 (m, 5H), 1.85–1.93 (m, 1H), 2.15–2.23 (m, 1H), 2.55–2.88 (m, 6H), 3.01–3.12 (m, 1H), 4.05–4.16 (m, 1H), 5.07 (d, J=5.3 Hz, 1H), 6.56 (s, 1H), 6.89–7.00 (m, 2H), 7.17–7.34 (m, 7H), 10.61 (s, 1H); MS (APCI$^+$), m/z 441 (MH$^+$).

EXAMPLE 13

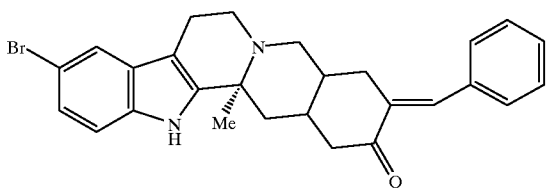

[4aR-[(E),4aα,13β,14aβ]]-3-Benzylidine-10-bromo-13b-methyl-3,4,4a,5,7,8,13,13b,14,14a-decahydro-1H-indolo[2',3':3,4]pyrido[1,2-b]-isoquinolin-2-one A solution of [2R-(2α,4aα,13β,14aβ)]-13b-methyl-1,2,3,4,4a,5,7,8,13,13b,14,14a-dodecahydro-indolo[2',3':3,4]pyrido[1,2-b]-isoquinolin-2-ol (1.5 g, 4.8 mmol; Zinnes H., Comes R. A., and Shavel J., Jr., *J. Org. Chem.*, 1965;30: 105) in 12 mL of methanol and 12 mL of acetic acid was treated dropwise with a solution of bromine (0.29 mL, 0.90 g, 5.6 mmol) in 3.0 mL of acetic acid. The mixture was stirred for 15 minutes, then condensed 50% without external heating. The residue was treated with 50 mL of diethyl ether and stirred for 15 minutes. The precipitated solid was filtered and washed several times with fresh ether. The solid was partitioned between 100 mL of ammonium hydroxide solution plus 200 mL of water and 150 mL of chloroform. The layers were separated, and the aqueous layer was extracted with fresh chloroform. The combined organic layers were washed with brine, dried ($Na_2SO_4$), and evaporated to yield 1.9 g of brominated intermediate as a mixture of isomers.

The above intermediate was oxidized with dimethyl sulfoxide and oxalyl chloride following the procedure described in Example 4. The resulting mixture of ketones was condensed with benzaldehyde following the procedure described in Example 7. The final product was purified by flash chromatography (40:60:1 ethyl acetate/hexane/triethylamine) to yield 0.14 g (6% overall yield) of the title compound;

$^1$H NMR (DMSO-$d_6$) δ 0.73–0.91 (m, 1H), 1.05–1.38 (m, 6H), 1.53–1.70 (m, 1H), 1.90–2.19 (m, 3H), 2.53–2.97 (m, 6H), 6.95–7.03 (m, 1H), 7.13–7.50 (m, 8H), 10.89 (s, 1H); MS (APCI$^+$), m/z 477 (M+2)$^+$.

EXAMPLE 14

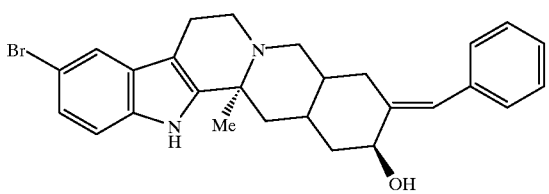

[2R-[2α(E),4aα,13bβ,14aβ]]-3-Benzylidine-10-bromo-13b-methyl-1,2,3,4,4a,5,7,8,13,13b,14,14a-dodecahydro-indolo[2',3':3,4]pyrido[1,2-b]-isoquinolin-2-ol Prepared in 64% yield from [4aR-[(E),4aα,13bβ,14aβ]]-3-benzylidene-10-bromo-13b-methyl-3,4,4a,5,7,8,13,13b,14,14a-decahydro-1H-indolo[2',3':3,4]-pyrido[1,2-b]isoquinolin-2-one by the procedure described in Example 10. The crude product was purified by flash chromatography (50:50:1 ethyl acetate/hexane/triethylamine) to yield the title compound;

$^1$H NMR (DMSO-$d_6$) δ 0.77–0.92 (m, 1H), 1.12–1.37 (m, 5H), 1.58–1.82 (m, 2H), 1.91–2.07 (m, 2H), 2.48–2.92 (m, 7H), 4.08–4.18 (m, 1H), 5.11 (d, J=5.4 Hz, 1H 6.57 (s, 1H), 7.04 (d, J=8.6 Hz, 1H), 7.15–7.42 (m, 8H), 10.91 (s, 1H); MS (APCI$^+$), m/z 479 (M+2)$^+$.

EXAMPLE 15

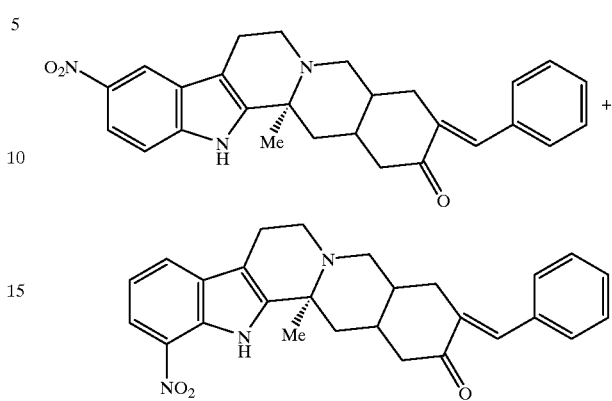

[4aR-[(E),4aα,13bβ,14aβ]]-3-Benzylidine-13b-methyl-10-nitro-3,4,4a,5,7,8,13,13b,14,14a-decahydro-1H-indolo[2',3':3,4]pyrido[1,2-b]-isoquinolin-2-one, and

[4aR-[(E),4aα,13bβ,14aβ]]-3-Benzylidine-13b-methyl-12-nitro-3,4,4a,5,7,8,13,13b,14,14a-decahydro-1H-indolo[2',3':3,4]pyrido[1,2-b]-isoquinolin-2-one A solution of [2R-(2α,4aα,13β,14aβ)]-13b-methyl-1,2,3,4,4a,5,7,8,13,13b,14,14a-dodecahydro-indolo[2',3':3,4]pyrido[1,2-b]-isoquinolin-2-ol (1.4 g, 4.5 mmol; Zinnes H., Comes R. A., and Shavel J., Jr., *J. Org. Chem.*, 1965;30: 105) in 10 mL of acetic acid was treated dropwise over 30 seconds with a mixture of 2.4 mL of acetic acid and 2.4 mL (3.8 g, 60 mmol) of fuming nitric acid. The mixture was stirred for 2 minutes, then poured over 40 g of ice and water. Concentrated ammonium hydroxide solution was added until the reaction mixture had a pH of 5.0. A solution of potassium nitrate was added to precipitate the product as the nitric acid salt. The aqueous layer was decanted from the precipitated salt, and the residue was dissolved in methanol. The solution was treated with ammonium hydroxide to precipitate the nitrated intermediate (0.96 g, 60%) as a mixture of 10- and 12-nitro isomers.

A solution of the above isomer mixture (0.90 g, 3.1 mmol) in 6.0 mL of dichloromethane was treated with 4-methylmorpholine N-oxide (0.46 g, 3.9 mmol), tetrapropylammonium perruthenate (0.18 g, 0.51 mmol), and 4Å powdered molecular sieves (1.5 g). The mixture was stirred for 4 hours at room temperature, and the solvent was evaporated. The residue was purified by flash chromatography (80:20 chloroform/acetone) to yield 0.45 g (41%) of an isomeric mixture of nitro ketones.

A solution of the above isomer mixture (0.44 g, 1.2 mmol) in 1.0 mL of methanol and 6.0 mL of tetrahydrofuran was treated with 0.6 ML of 10% aqueous sodium hydroxide solution. The mixture was heated to reflux, and a solution of benzaldehyde (0.29 mL, 0.30 g, 2.9 mmol) in 4.0 mL of tetrahydrofuran was added dropwise. Heating at reflux was continued for 16 hours. The cooled reaction mixture was evaporated, and the residue was partitioned between ethyl acetate and brine. The organic layer was dried ($MgSO_4$) and evaporated. Purification of the residue by flash chromatography (60:30:10 ethyl acetate/hexane (triethylamine) gave 0.078 g (14%) of [4aR-[(E),4aα,13bβ,14aβ]]-3-benzylidine-13b-methyl-10-nitro-3,4,4a,5,7,8,13,13b,14,14a-decahydro-1H-indolo[2',3':3,4]pyrido[1,2-b]-isoquinolin-2-one;

$^1$H NMR (DMSO-$d_6$) δ 0.75–0.97 (m, 1H), 1.08–1.15 (m, 2H), 1.32 (s, 3H), 1.35-1.47 (m, 1H), 1.58–1.80 (m, 1H), 2.03–2.22 (m, 3H), 2.40–2.91 (m, 6H), 7.10–7.52 (m, 7H), 7.80 (d, J=8.8 Hz, 1H), 8.13 (s, 1H), 11.61 (s, 1H); MS (APCI⁺), m/z 442 (MH⁺), and 0.066 g (12%) of [4aR-[(E),4aα,13bβ,14aβ]]-3-benzylidine-13b-methyl-12-nitro-3,4,4a,5,7,8,13,13b,14,14a-decahydro-1H-indolo[2',3':3,4]pyrido[1,2-b]-isoquinolin-2-one;

¹H NMR (DMSO-d₆) δ 0.75–0.88 (m, 1H), 1.04–1.45 (m, 6H), 1.58–1.89 (m, 2H), 1.96–2.28 (m, 2H), 2.57–2.93 (m, 4H), 3.07–3.18 (m, 2H), 7.06–7.11 (m, 1H), 7.30–7.52 (m, 5H), 7.61–7.83 (m, 2H), 8.12 (s, 1H), 11.68 (s, 1H); MS (APCI⁺), m/z 442 (MH⁺).

EXAMPLE 16

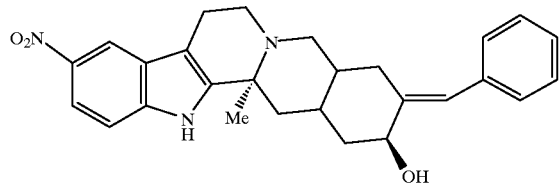

[2R-[2α(E),4aα,13bβ,14aβ]]-3-Benzylidine-13b-methyl-10-nitro-1,2,3,4,4a,5,7,8,13,13b,14,14a-dodecahydro-indolo[2',3':3,4]pyrido[1,2-b]-isoquinolin-2-ol A solution of [4aR-[(E),4aα,13bβ,14aβ]]-3-benzylidene-13b-methyl-10-nitro-3,4,4a,5,7,8,13,13b,14,14a-decahydro-1H-indolo[2',3':3,4]pyrido[1,2-b]-isoquinolin-2-one (0.071 g, 0.16 mmol) in 5.0 mL of tetrahydrofuran and 1.0 mL of methanol was cooled in an ice bath and treated slowly with sodium borohydride (0.031 g, 0.82 mmol). The mixture was stirred at room temperature for 16 hours, then cooled in ice and treated with 1.0 mL of water and 4.0 mL of acetic acid. The pH of the mixture was adjusted to 9.0 by the addition of ammonium hydroxide solution. The mixture was extracted with chloroform, and the combined extracts were washed with brine, dried (MgSO₄), and evaporated. The residue was recrystallized from methanol to yield 0.048 g (68%) of product;

¹H NMR (CDCl₃) δ 1.12–1.25 (m, 1H), 1.39 (s, 3H), 1.40–1.78 (m, 4H), 1.83–1.92 (m, 1H), 2.00 (s, 1H), 2.04–2.13 (m, 1H), 2.52–3.05 (m, 7H), 4.21–4.32 (m, 1H), 6.61 (s, 1H), 7.08–7.35 (m, 5H), 7.42 (d, J=8,6 Hz, 1H), 7.95 (m, 1H), 8.23 (s, 1H), 8.45 (s, 1H); MS (APCI⁺), m/z 444 (MH⁺).

EXAMPLE 17

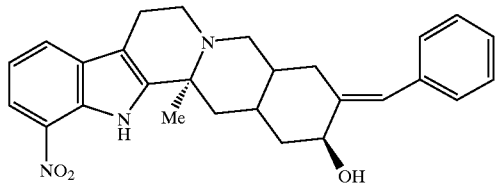

[2R-[2α(E),4aα,13bβ,14aβ]]-3-Benzylidine-13b-methyl-12-nitro-1,2,3,4,4a,5,7,8,13,13b,14,14a-dodecahydro-indolo[2',3':3,4]pyrido[1,2-b]-isoquinolin-2-ol Prepared in 29% yield from [4aR-[(E),4aα,13bβ,14aβ]]-3-benzylidene-13b-methyl-12-nitro-3,4,4a,5,7,8,13,13b,14,14a-decahydro-1H-indolo[2',3':3,4]pyrido[1,2-b]isoquinolin-2-one by the procedure described in Example 16. The final product was recrystallized from methanol;

¹H NMR (CDCl₃) δ 1.11–1.23 (m, 1H), 1.35 (s, 3H), 1.38–2.14 (m, 7H), 2.43–2.69 (m, 2H), 2.73–2.92 (m, 3H), 3.03–3.16 (m, 1H), 3.43 (s, 1H), 4.20–4.30 (m, 1H), 6.57 (s, 1H), 7.02–7.33 (m, 6H), 7.49 (d, J=8.1 Hz, 1H), 7.82 (d, J=8.1 Hz, 1H), 8.08 (s, 1H); MS (APCI⁺), m/z 444 (MH⁺).

EXAMPLE 18

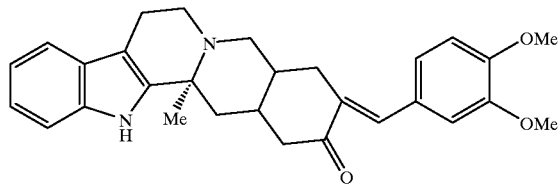

[4aR-[(E),4a,13bβ,14aβ]]-3-(3,4-Dimethoxy-benzylidene)-13b-methyl-3,4,4a,5,7,8,13,13b,14,14a-decahydro-1H-indolo[2',3':3,4]pyrido[1,2-b]-isoquinolin-2-one To a solution of [4aR-(4aα,13bβ,14aβ)]-13b-methyl-3,4,4a,5,7,8,13,13b,14,14a-decahydro-1H-indolo[2',3':3,4]pyrido[1,2-b]-isoquinolin-2-one (0.25 g, 0.81 mmol; Zinnes H., Comes R. A., and Shavel J., Jr., *J. Org. Chem.*, 1965;30:105) in 15 mL of methanol was added 3,4-dimethoxybenzaldehyde (0.61 g, 3.7 mmol), followed by 0.30 mL of 10% aqueous sodium hydroxide solution. The mixture was stirred at reflux for 18 hours. The solvent was evaporated, and the residue was dissolved in a minimum amount of dichloromethane and purified by flash chromatography (70:30 ethyl acetate/hexane) to yield 0.17 g (47%) of the benzylidene ketone of mp 120–125° C.;

¹H NMR (CDCl₃) δ 1.34 (s, 3H), 1.54 (t, J=12.1 Hz, 1H), 1.70–1.88 (m, 1H), 1.88–2.15 (m, 3H), 2.27–2.39 (m, 1H), 2.54–2.76 (m, 4H), 2.79–3.04 (m, 4H), 3.82 (s, 3H), 3.85 (s, 3H), 6.84 (d, J=8.4 Hz, 1H), 6.88 (s, 1H), 6.96–7.09 (m 3H), 7.23 (d, J=7.9 Hz, 1H), 7.39 (d, J=7.5 Hz, 1H), 7.47 (s, 1H), 7.81 (s, 1H); MS (APCI⁺), m/z 457 (MH⁺).

EXAMPLE 19

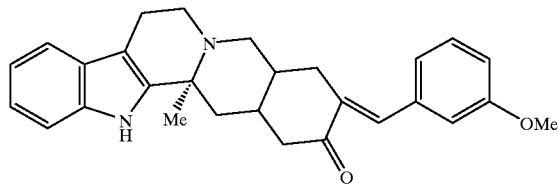

[4aR-[(E),4aα,13bβ,14aβ]]3-(3-Methoxy-benzylidene)-13b-methyl-3,4,4a,5,7,8,13,13b,14,14a-decahydro-1H-indolo[2',3':3,4]pyrido[1,2-b]-isoquinolin-2-one Prepared in 46% yield from [4aR-(4aα,13bβ,14aβ)]-13b-methyl-3,4,4a,5,7,8,13,13b,14,14a-decahydro-1H-indolo[2',3':3,4]pyrido[1,2-b]-isoquinolin-2-one and 3-methoxybenzaldehyde by the procedure described in Example 18. The product had mp 125–130° C.;

¹H NMR (CDCl₃) δ 1.10–1.25 (m, 1H), 1.35 (s, 3H), 1.45–3.05 (m, 13H), 3.75 (s, 3H), 6.75–7.50 (m, 9H), 7.75 (s, 1H); MS (APCI⁺), m/z 427 (MH⁺).

EXAMPLE 20

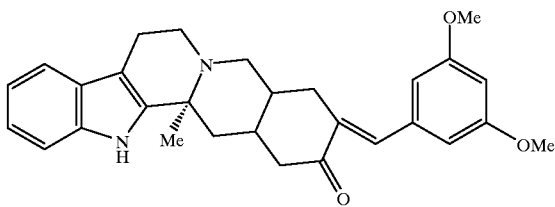

[4aR-[(E),4aα,13bβ,14aβ]]-3-(3,5-Dimethoxy-benzylidene)-13b-methyl-3,4,4a,5,7,8,13,13b,14,14a-decahydro-1H-indolo[2',3':3,4]pyrido[1,2-b]-isoquinolin-2-one Prepared in 44% yield from [4aR-(4aα,13bβ,14aβ)]-13b-methyl-3,4,4a,5,7,8,13,13b,14,14a-decahydro-1H-indolo[2',3':3,4]pyrido[1,2-b]-isoquinolin-2-one and 3,5-dimethoxybenzaldehyde by the procedure described in Example 18. The product had mp 110–120° C.;
$^1$H NMR (CDCl$_3$) δ 1.37 (s, 3H), 1.47–1.69 (m, 1H), 1.73–1.89 (m, 1H, 1.91–2.25 (m, 3H), 2.25–2.41 (m, 1H), 2.56–2.79 (m, 4H), 2.79–3.14 (m, 4H), 3.78 (s, 6H), 6.43 (s, 1H) 6.50 (s, 2H), 6.99–7.20 (m, 2H), 7.27 (d, J=8.0 Hz, 1H), 7.42 (s, 2H), 7.66 (s, 1H); MS (APCI$^+$), m/z 457 (MH$^+$).

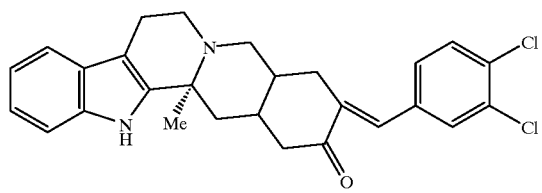

EXAMPLE 21

[4aR-[(E),4aα,13bβ,14aβ]]-3-(3,4-Dichloro-benzylidene)-13b-methyl-3,4,4a,5,7,8,13,13b,14,14a-decahydro-1H-indolo[2',3':3,4]pyrido[1,2-b]-isoquinolin-2-one Prepared in 17% yield from [4aR-(4aα,13bβ,14aβ)]-13b-methyl-3,4,4a,5,7,8,13,13b,14,14a-decahydro-1H-indolo[2',3':3,4]pyrido[1,2-b]-isoquinolin-2-one and 3,4-dichlorobenzaldehyde by the procedure described in Example 18. The product had mp 140–145° C.;
$^1$H NMR (CDCl$_3$) δ 1.34 (s, 3H), 1.57 (t, J=12.0 Hz, 1H), 1.71–1.88 (m, 1H), 1.88–2.17 (m, 3H), 2.21–2.37 (m, 1H,), 2.54–2.78 (m, 4H), 2.78–3.05 (m, 4H), 7.02 (t, J=7.6 Hz, 1H), 7.08 (t, J=7.2 Hz, 1H), 7.15 (dd, J=8.6, 1.7 Hz, 1H), 7.24 (d, J=7.9 Hz, 1H), 7.30–7.46 (m, 4H), 7.61 (s, 1H); MS (APCI$^+$), m/z 465 (MH$^+$).

EXAMPLE 22

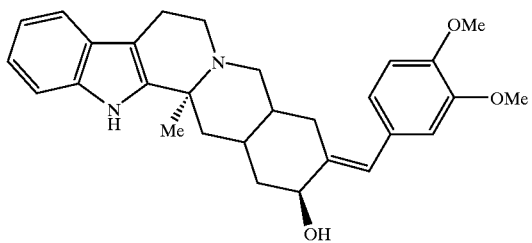

[2R-[2α(E),4aα,13bβ,14aβ]]-3-(3,4-Dimethoxy-benzylidene)-13b-methyl-1,2,3,4,4a,5,7,8,13,13b,14,14a-dodecahydro-indolo[2',3':3,4]pyrido[1,2-b]-isoquinolin-2-ol A solution of [4aR-[(E),4aα,13bβ,14aβ]]-3-(3,4-dimethoxy-benzylidene)-13b-methyl-3,4,4a,5,7,8,13,13b,14,14a-decahydro-1H-indolo[2',3':3,4]-pyrido[1,2-b]-isoquinolin-2-one (0.15 g, 0.34 mmol) in 2.0 mL of methanol and 4.0 mL of tetrahydrofuran was treated with potassium borohydride (0.09 g, 1.7 mmol). The mixture was stirred at room temperature for 18 hours. The solvent was evaporated, and the residue was suspended in 3.0 mL of water and treated with 4.0 mL of glacial acetic acid. The solution was allowed to stir at room temperature for 30 minutes, and then 5.0 mL of ammonium hydroxide was added until pH 8. The precipitated product was extracted with chloroform. The organic layer was dried (Na$_2$SO$_4$) and evaporated to yield an oil. The residue was purified by flash chromatography (95:5 chloroform/methanol) to yield 0.10 g (68%) of product of mp 118–121° C.;
$^1$H NMR (CDCl$_3$) δ 1.08–1.17 (m, 1H), 1.31 (s, 3H), 1.37–1.76 (m, 4H), 1.79 (dd, J=12.1, 3.3 Hz, 1H), 2.01–2.10 (m, 1H), 2.11 (s, 1H), 2.50–2.70 (m, 3H), 2.76–2.98 (m, 4H), 3.80 (s, 3H), 3.82 (s, 3H), 4.22 (dd, J=11.3, 3.5 Hz, 1H), 6.50 (s, 1H), 6.61–6.73 (m, 2H), 6.73–6.82 (d, J=8.3 Hz, 1H), 7.01 (t, J=7.6 Hz, 1H), 7.07 (t, J=7.6 Hz, 1H), 7.23 (d, J=8.0 Hz, 1H), 7.39 (d, J=8.0 Hz, 1H), 7.61 (s, 1H); MS (APCI$^+$), m/z 459 (MH$^+$).

EXAMPLE 23

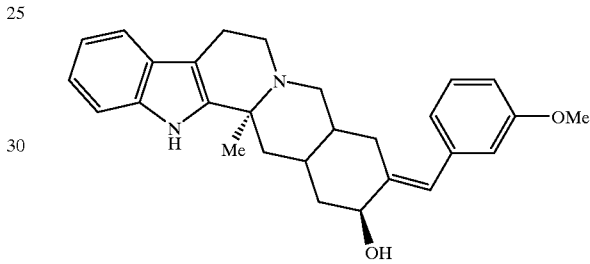

[2R-[2α(E),4aα,13bβ,14aβ]]-3-(3-Methoxy-benzylidene)-13b-methyl-1,2,3,4,4a,5,7,8,13,13b,14,14a-dodecahydro-indolo[2',3':3,4]pyrido[1,2-b]-isoquinolin-2-ol Prepared in 21% yield from [4aR-[(E),4aα,13bβ,14aβ]]-3-(3-methoxy-benzylidene)-13b-methyl-3,4,4a,5,7,8,13,13b,14,14a-decahydro-1H-indolo[2',3':3,4]pyrido[1,2-b]isoquinolin-2-one by the procedure described in Example 22. The product had mp 140–142° C.;
$^1$H NMR (CDCl$_3$) δ 1.16 (m, 1H), 1.35 (s, 3H), 1.40–1.70 (m, 4H), 1.75 (dd, J=12.0, 3.3 Hz, 1H), 2.00–2.10 (m, 2H), 2.54–2.74 (m, 3H), 2.80–3.03 (m, 4H, CH$_2$), 3.80 (s, 3H), 4.25 (dd, J=11.2, 4.3 Hz, 1H), 6.61 (s, 1H), 6.70–6.87 (m, 3H), 7.04–7.19 (m, 2H), 7.19–7.28 (m, 1H), 7.31 (d, J=7.9 Hz, 1H), 7.47 (d, J=7.7 Hz, 1H), 7.75 (s, 1H); MS (APCI$^+$), m/z 429 (MH$^+$).

EXAMPLE 24

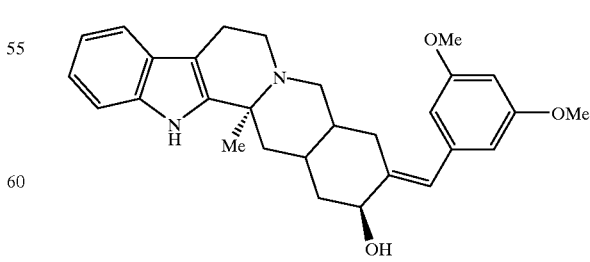

[2R-[2α(E),4aα,13bβ,14aβ,]]-3-(3,5-Dimethoxy-benzylidene)-13b-methyl-1,2,3,4,4a,5,7,8,13,13b,14,14a-dodecahydro-indolo[2',3':3,4]pyrido[1,2-b]-isoquinolin-2-ol Prepared in 50% yield from [4aR-[(E),4aα,13bβ,14aβ]]-3-(3,5-dimethoxy-benzylidene)-13b-methyl-3,4,4a,5,7,8,13,13b,14,14a-decahydro-1H-indolo[2',3':3,4]pyrido[1,2-b]isoquinolin-2-one by the procedure described in Example 22. The product had mp 128–132° C.;

$^1$H NMR (CDCl$_3$) δ 1.10–1.19 (m, 1H), 1.33 (s, 3H), 1.38–2.00 (m, 5H), 2.02–2.12 (m, 1H), 2.14 (s, 1H), 2.50–2.74 (m, 3H), 2.75–3.04 (m, 4H), 3.75 (s, 6H), 4.24 (dd, J=11.3, 3.5 Hz, 1H), 6.32 (s, 3H), 6.53 (s, 1H), 7.04 (t, J=7.7 Hz 1H), 7.10 (t, J=7.4 Hz, 1H), 7.26 (d, J=8.3 Hz, 1H), 7.42 (d, J=7.5 Hz, 1H), 7.65 (s, 1H); MS (APCI$^+$), m/z 459 (MH$^+$).

EXAMPLE 25

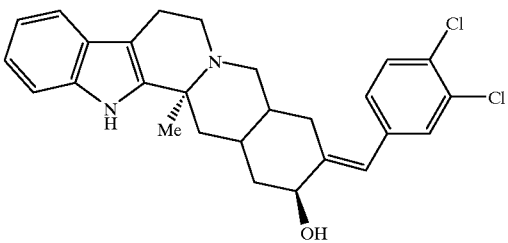

[2R-[2α(E),4aα,13bβ,14aβ]]-3-(3,4-Dichloro-benzylidene)-13b-methyl-1,2,3,4,4a,5,7,8,13,13b,14,14a-dodecahydro-indolo[2',3':3,4]pyrido[1,2-b]-isoquinolin-2-ol Prepared in 44% yield from [4aR-[(E),4aα,13bβ,14aβ]]-3-(3,4-dichloro-benzylidene)-13b-methyl-3,4,4a,5,7,8,13,13b,14,14a-decahydro-1H-indolo[2',3':3,4]pyrido[1,2-b]isoquinolin-2-one by the procedure described in Example 22. The product had mp 125–130° C.;

$^1$H NMR (CDCl$_3$) δ 1.06–1.17 (m, 1H), 1.31 (s, 3H), 1.34–1.86 (m, 5H), 2.03–2.10 (m, 1H), 2.11 (s, 1H), 2.50–2.70 (m, 3H), 2.76–2.99 (m, 4H), 4.22 (dd, J=11.7, 3.8 Hz, 1H), 6.47 (s, 1H), 6.94 (dd, J=8.2, 1.9 Hz, 1H), 7.01 (t, J=7.7 Hz, 1H), 7.07 (t, J=8.0 Hz, 1H), 7.16–7.27 (m, 2H), 7.32 (d, J=8.3 Hz, 1H), 7.39 (d, J=7.3 Hz, 1H), 7.59 (s, 1H); MS (APCI$^+$), m/z 467 (MH$^+$).

EXAMPLE 26

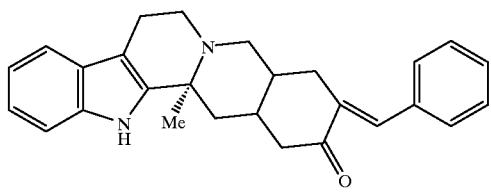

[4aR-[(E),4aα,13bβ,14aβ]]-3-Benzylidene-13b-methyl-3,4,4a,5,7,8,13,13b,14,14a-decahydro-1H-indolo[2',3':3,4]pyrido[1,2-b]-isoquinolin-2-one Prepared in 50% yield from [4aR-(4aα,13bβ,14aβ)]-13b-methyl-3,4,4a,5,7,8,13,13b,14,14a-decahydro-1H-indolo[2',3':3,4]pyrido[1,2-b]-isoquinolin-2-one and benzaldehyde by the procedure described in Example 18. The product had mp 135–145° C.;

$^1$H NMR (CDCl$_3$) δ 1.38 (s, 3H), 1.53–1.65 (m, 1H), 1.75–1.89 (m, 1H), 1.92–2.18 (m, 3H), 2.29–2.43 (m, 1H), 2.56–2.79 (m, 4H), 2.79–3.09 (m, 4H), 7.01–7.15 (m, 2H), 7.20–7.49 (m, 7H), 7.52 (s, 1H), 7.67 (s, 1H); MS (APCI$^+$), m/z 397 (MH$^+$).

EXAMPLE 27

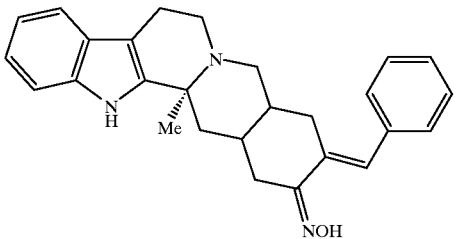

[4aR-[(E),4aα,13bβ,14aβ]]-3-Benzylidene-13b-methyl-3,4,4a,5,7,8,13,13b,14,14a-decahydro-1H-indolo[2',3':3,4]pyrido[1,2-b]-isoquinolin-2-one oxime A solution of [4aR-[(E),4aα,13bβ,14aβ]]-3-benzylidene-13 b-methyl-3,4,4a,5,7,8,13,13b,14,14a-decahydro-1H-indolo[2',3':3,4]pyrido[1,2-b]-isoquinolin-2-one (0.12 g, 0.31 mmol) in 4.0 mL of ethanol and 4.0 mL of water was treated with hydroxylamine hydrochloride (0.13 g, 1.9 mmol), followed by sodium acetate hydrate (0.25 g, 1.9 mmol). The mixture was stirred at reflux for 18 hours. The solvent was evaporated, and the residue was suspended in water and extracted with chloroform. The organic layer was dried (Na$_2$SO$_4$) and evaporated to afford a solid. The crude product was purified by flash chromatography (40:60 ethyl acetate/hexane) to yield 0.067 g (53%) of product of mp 142–145° C.;

$^1$H NMR (CDCl$_3$) δ 1.32 (s, 3H), 1.47–3.33 (m, 15H), 6.87 (s, 1H), 7.01 (t, J=78 Hz, 1H), 7.07 (t, J=7.2 Hz, 1H), 6.95–7.12 (m, 6H), 7.39 (d, J=7.6 Hz, 1H), 7.61 (s, 1H); MS (APCI$^+$), m/z 412 (MH$^+$).

EXAMPLE 28

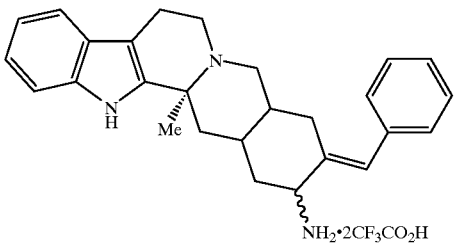

3-Benzylidene-13b-methyl-1,2,3,4,4a,5,7,8,13,13b,14,14a-dodecahydro-indolo[2',3':3,4]pyrido[1,2-blisoquinolin-2-ylamine A solution of [4aR-[(E),4aα,13bβ,14aβ]]-3-benzylidene-13b-methyl-3,4,4a,5,7,8,13,13b,14,14a-decahydro-1H-indolo[2',3':3,4]pyrido[1,2-b]-isoquinolin-2-one oxime (0.12 g, 0.29 mmol) in 5.0 mL of ethanol and 5.0 mL of glacial acetic acid was cooled to 0° C. and treated with zinc dust (0.19 g, 2.9 mmol). The mixture was warmed to room temperature and stirred for 3 hours. The mixture was filtered, and the zinc was washed with fresh ethanol. The solvent was evaporated, and the residue was suspended in 10.0N sodium hydroxide solution and extracted with chloroform. The organic layer was separated, dried (Na$_2$SO$_4$), and the solvent was evaporated to afford a solid. The crude product was purified by preparative HPLC (acetonitrile/water+0.05% trifluoroacetic acid gradient elution) to yield 0.025 g (14%) of final product as the di-trifluoroacetic acid salt; mp 203–210° C.;

MS (APCI$^+$), m/z 398 (MH$^+$).

The following were prepared by the above procedures:

[1R-[1α,2β(E),4aβ,13bα,14aα]]3-Benzylidene-1,13b-dimethyl-1,2,3,4,4a,5,7,8,13,13b,14,14a-dodecahydro-indolo[2',3':3,4]pyrido]1,2-b]isoquinolin-3-ol;

[1R-[1α,2β(E),4aβ,13bα,14aα]]3-Biphenyl-4-ylmethylene-1,13b-dimethyl-1,2,3,4,4a,5,7,8,13,13b,14,14a-dodecahydro-indolo[2',3':3,4]pyrido]1,2-b]isoquinolin-2-ol; and

[1R-[1α,2β(E),4aβ,13bα,14aα]]1,13b-Dimethyl-3-(4-styryl-benzylidene)-1,2,3,4,4a,5,7,8,13,13b,14,14a-dodecahydro-indolo[2',3':3,4]pyrido]1,2-b]isoquinolin-2-ol.

What is claimed is:

1. A compound of Formula I

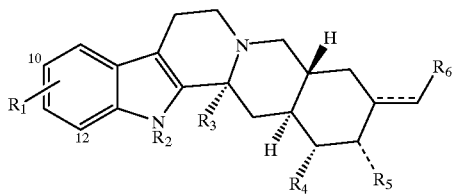

I or a pharmaceutically acceptable salt thereof wherein:

the --- represents an optional double bond;

$R_1$ is hydrogen, lower alkyl, lower alkenyl, alkoxy, hydroxy, halogen, $CH_2OH$, trifluoromethyl, nitro, cyano, amino, substituted amino, or $(CH_2)_m$—COOR wherein m is an integer of from 0 to 2 and R is alkyl or hydrogen;

$R_2$ is hydrogen or lower alkyl;

$R_3$ is lower alkyl, lower alkenyl, benzyl, or aryl;

$R_4$ is hydrogen, lower alkyl, —COOR, —CONHR wherein R is hydrogen, alkyl, or aryl;

$R_5$ is hydroxyl, amino, or carbonyl; and $R_6$ is phenyl, substituted phenyl, naphthyl, or a heterocycle selected from the group consisting of pyrimidine, pyridazine, quinazoline, and quinazolinone with the proviso that $R_3$ is not methyl when $R_4$ is hydrogen, $R_5$ is hydroxy, and $R_6$ is phenyl.

2. A compound according to claim 1 of formula

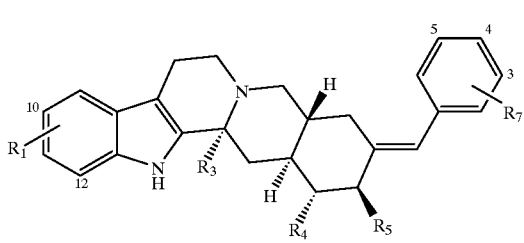

IA wherein $R_1$ is hydrogen, bromine, or nitro;

$R_3$ is methyl, n-propyl, n-butyl, or allyl;

$R_4$ is hydrogen or methyl;

$R_5$ is hydroxy, NOH, or $NH_2$;

$R_7$ is hydrogen, 3,4-methoxy, 3-methoxy, 3,5-methoxy, 3,4-chloro, 4-phenyl, or 4—

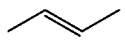

phenyl with the proviso that $R_3$ is not methyl when $R_4$ and $R_7$ are hydrogen, and $R_5$ is hydroxy.

3. A compound according to claim 1, wherein said compound is [2S-(2α, 4aα, 13β, 14aβ)]-13b-Allyl-3-1, 2, 3, 4, 4a, 5, 7, 8, 13, 13b, 14, 14a-dodecahydro- indolo[2', 3':3, 4]pyrido[1,2-b]isoquinolin-2-ol.

4. A compound of claim 1, wherein said compound is [2S-(2α, 4aα, 13β, 14aβ)]-3-Benzylidine-13b- propyl-1, 2, 3, 4, 4a, 5, 7, 8, 13, 13b, 14, 14a- dodecahydro-indolo[2', 3':3, 4]pyrido[1,2-b]isoquinolin-2-ol.

5. A compound of claim 1, wherein said compound is [2S-(2α, 4aα, 13β, 14aβ)]-3-Benzylidine-13b-propyl-1, 2, 3, 4, 4a, 5, 7, 8, 13, 13b, 14, 14a- dodecahydro-indolo[2', 3':3, 4]pyrido[1,2-b]isoquinolin-2-ol.

6. A compound of claim 1, wherein said compound is [2R-[2α(E), 4aα, 13bβ, 14aβ]]-3-Benzylidine-10-bromo-13b methyl-1, 2, 3, 4, 4a, 5, 7, 8, 13, 13b, 14, 14a-dodecahydro-indolo[2', 3':3,4]pyrido[1,2-b]isoquinolin-2-ol.

7. A compound of claim 1, wherein said compound is [2R-[2α(E), 4aα, 13bβ, 14aβ]]-3-Benzylidine-13b-methyl-10-nitro-1, 2, 3, 4, 4a, 5, 7, 8, 13, 13b, 14, 14a- dodecahydro-indolo[2', 3':3, 4]pyrido[1,2-b]isoquinolin-2-ol.

8. A compound of claim 1, wherein said compound is [2R-[2α(E), 4aα, 13bβ, 14aβ]]-3-Benzylidine-13b-methyl-12-nitro-1, 2, 3, 4, 4a, 5, 7, 8, 13, 13b, 14, 14a- dodecahydro-indolo[2', 3':3, 4]pyrido[1,2-b]isoquinolin-2-ol.

9. A compound of claim 1, wherein said compound is [2R-[2α(E), 4aα, 13bβ, 14aβ]]-3-(3,4-Dimethoxy-benzylidene)-13b-methyl-1, 2, 3, 4, 4a, 5, 7, 8, 13, 13b, 14, 14a- dodecahydro-indolo[2', 3':3, 4]pyrido[1,2-b]isoquinolin-2-ol.

10. A compound of claim 1, wherein said compound is [2R-[2α(E), 4aα, 13bβ, 14aβ]]-3-(3,4-Methoxy-benzylidene)-13b-methyl-1, 2, 3, 4, 4a, 5, 7, 8, 13, 13b, 14, 14a- dodecahydro-indolo[2', 3':3, 4]pyrido[1,2-b]isoquinolin-2-ol.

11. A compound of claim 1, wherein said compound is [2R-[2α(E), 4aα, 13bβ, 14aβ]]-3-(3,5-Dimethoxy-benzylidene)-13b-methyl-1, 2, 3, 4, 4a, 5, 7, 8, 13, 13b, 14, 14a- dodecahydro-indolo[2', 3':3, 4]pyrido[1,2-b]isoquinolin-2-ol.

12. A compound of claim 1, wherein said compound is [2R-[2α(E), 4aα, 13bβ, 14aβ]]-3-(3,4-Dichloro-benzylidene)-13b-methyl-1, 2, 3, 4, 4a, 5, 7, 8, 13, 13b, 14, 14a- dodecahydro-indolo[2', 3':3, 4]pyrido[1,2-b]isoquinolin-2-ol.

13. A compound of claim 1, wherein said compound is 3-Benzlidene-13b- methyl- 1, 2, 3, 4, 4a, 5, 7, 8, 13, 13b, 14, 14a-dodecahydro-indolo [2', 3':3, 4]pyrido[1,2-b]isoquinolin-2-ylamine.

14. A compound of claim 1, wherein said compound is [1R- [1α,2β(E), 4aα, 13βα, 14α]]1,13b-Dimethyl-3-(4-stryryl-benzylidene)- 1, 2, 3, 4, 4a, 5, 7, 8, 13, 13b, 14, 14a-dodecahydro-indolo [2', 3':3, 4]pyrido[1,2-b]isoquinolin-2-ol.

15. A compound of claim 1, wherein said compound is [1R-[1α,2β(E),4aβ, 13βα, 14aα]]3-Benzylidene-1,13b-dimethyl- 1, 2, 3, 4, 4a, 5, 7, 8, 13, 13b, 14, 14a-dodecahydro-indolo[2',3':3,4]pyrido[1,2-b]isoquinolin-3-ol.

16. A compound of claim 1, wherein said compound is [1R- [1R-[1α,2β(E),4aβ, 13βα, 14aα]]3-Biphenyl-4-ylmethylene-1, 13b-dimethyl- 1, 2, 3, 4, 4a, 5, 7, 8, 13, 13b, 14, 14a-dodecahydro-indolo[2',3':3,4]pyrido[1,2-b]isoquinolin-3-ol.

17. A compound of claim 1, wherein said compound is [4aS- (2E,4aα, 13β, 14aβ]-13b-Allyl-3-benzylidene- 3, 4, 4a, 5, 7, 8, 13, 13b, 14, 14a-decahydro- 1H-indolo[2',3':3,4]pyrido[1,2-b]isoquinolin-2-one.

18. A compound of claim 1, wherein said compound is [4aS- (2E,4aα, 13β, 14aβ]-3-Benzylidene-13b-propyl- 3, 4, 4a, 5, 7, 8, 13, 13b, 14, 14a-decahydro- 1H-indolo[2',3':3,4]pyrido[1,2-b]isoquinolin-2-one.

19. A compound of claim 1, wherein said compound is [4aS- (2E,4aα, 13β, 14aβ]-3-Benzylidene-13b-butyl- 3, 4, 4a, 5, 7, 8, 13, 13b, 14, 14a-decahydro- 1H-indolo[2',3':3,4]pyrido[1,2-b]isoquinolin-2-one.

20. A compound of claim 1, wherein said compound is [4aR- [(E),4aα, 13bβ, 14aβ]]-3-Benzylidene-10-bromo-13b-methyl- 3, 4, 4a, 5, 7, 8, 13, 13b, 14, 14a-decahydro-1H-indolo[2',3':3,4]pyrido[1,2-b]isoquinolin-2-one.

21. A compound of claim 1, wherein said compound is [4aR- [(E),4aα, 13bβ, 14aβ]]-3-Benzylidene-13-methyl-10-nitro- 3, 4, 4a, 5, 7, 8, 13, 13b, 14, 14a-decahydro- 1H-indolo[2',3':3,4]pyrido[1,2-b]isoquinolin-2-one.

22. A compound of claim 1, wherein said compound is [4aR- [(E),4aα, 13bβ, 14aβ]]-3-Benzylidene-13-methyl-12-nitro- 3, 4, 4a, 5, 7, 8, 13, 13b, 14, 14a-decahydro- 1H-indolo[2',3':3,4]pyrido[1,2-b]isoquinolin-2-one.

23. A compound of claim 1, wherein said compound is [4aR- [(E),4aα, 13bβ, 14aβ]]-3-(3,4-Dimethoxy-benzylidene)-13b-methyl- 3, 4, 4a, 5, 7, 8, 13, 13b, 14, 14a-decahydro- 1H-indolo[2',3':3,4]pyrido[1,2-b]isoquinolin-2-one.

24. A compound of claim 1, wherein said compound is [4aR- [(E),4aα, 13bβ, 14aβ]]3-(3-Methoxy-benzylidene)-13b-methyl- 3, 4, 4a, 5, 7, 8, 13, 13b, 14, 14a-decahydro-1H-indolo[2',3':3,4]pyrido[1,2-b]isoquinolin-2-one.

25. A compound of claim 1, wherein said compound is [4aR- [(E),4aα, 13bβ, 14aβ]]-3-(3,5-Dimethoxy-benzylidene)-13b-methyl- 3, 4, 4a, 5, 7, 8, 13, 13b, 14, 14a-decahydro- 1H-indolo[2',3':3,4]pyrido[1,2-b]isoquinolin-2-one.

26. A compound of claim 1, wherein said compound is [4aR- [(E),4aα, 13bβ, 14aβ]]-3-(3,4-Dichloro-benzylidene)-13b-methyl- 3, 4, 4a, 5, 7, 8, 13, 13b, 14, 14a-decahydro-1H-indolo[2',3':3,4]pyrido[1,2-b]isoquinolin-2-one.

27. A compound of claim 1, wherein said compound is [4aR- [(E),4aα, 13bβ, 14aβ]]-3-Benzylidene-13b-methyl-3, 4, 4a, 5, 7, 8, 13, 13b, 14, 14a-decahydro- 1H-indolo[2',3':3,4]pyrido[1,2-b]isoquinolin-2-one.

28. A method of treating inflammation in a mammal in need thereof comprising administering to said mammal an effective anti-inflammatory amount of a compound of any one of claims 1, 3, or 4–27.

29. A method of treating inflammation in a mammal in need thereof comprising administering to said mammal an effective anti-inflammatory amount of a compound of claim 2.

30. A method of treating pain in a mammal in need thereof comprising administering to said mammal an effective analgesic amount of a compound of any one of claims 1, 2, 4, or 26–49.

31. A pharmaceutical composition comprising a compound according to any one of claims 1, 3, or 4–27 in admixture with a pharmaceutically acceptable excipient, diluent, or carrier.

32. A pharmaceutical composition comprising a compound according to claim 2 in admixture with a pharmaceutically acceptable excipient, diluent, or carrier.

33. A method of inhibiting the binding of MCP-1 to its receptor comprising administering a therapeutically effective amount of compound according to any one of claims 1, 2, 3, or 4–27 to a mammal in need thereof.

* * * * *